(12) United States Patent
Jensen et al.

(10) Patent No.: US 7,232,562 B2
(45) Date of Patent: *Jun. 19, 2007

(54) E38N INTERFERON GAMMA POLYPEPTIDE VARIANTS

(75) Inventors: Anne Dam Jensen, Copenhagen (DK); Kim Vilbour Andersen, Broenshoej (DK); Christian Karsten Hansen, Vedback (DK)

(73) Assignee: Maxygen Holdings Ltd. (KY)

( * ) Notice: Subject to any disclaimer, the term of this patent is extended or adjusted under 35 U.S.C. 154(b) by 707 days.

This patent is subject to a terminal disclaimer.

(21) Appl. No.: 10/369,495

(22) Filed: Feb. 19, 2003

(65) Prior Publication Data

US 2003/0153046 A1 Aug. 14, 2003

Related U.S. Application Data

(63) Continuation of application No. 10/130,084, filed as application No. PCT/DK00/00631 on Nov. 13, 2000.

(60) Provisional application No. 60/166,293, filed on Nov. 18, 1999.

(30) Foreign Application Priority Data

| Nov. 12, 1999 | (DK) | ............ | PA 1999 01631 |
| Mar. 17, 2000 | (DK) | ............ | PA 2000 00447 |

(51) Int. Cl.
A61K 38/21 (2006.01)
A61K 39/00 (2006.01)
C07K 17/00 (2006.01)
C12P 21/04 (2006.01)

(52) U.S. Cl. .............. 424/85.5; 424/85.4; 424/185.1; 530/351; 435/69.51

(58) Field of Classification Search .................. None
See application file for complete search history.

(56) References Cited

U.S. PATENT DOCUMENTS

| 4,457,867 A | 7/1984 | Ishida |
| 4,588,585 A | 5/1986 | Mark et al. |
| 4,604,284 A | 8/1986 | Kung et al. |
| 4,695,623 A | 9/1987 | Stabinsky |
| 4,727,138 A | 2/1988 | Goeddel et al. |
| 4,758,656 A | 7/1988 | Itoh et al. |
| 4,762,791 A | 8/1988 | Goeddel et al. |
| 4,832,959 A | 5/1989 | Engels et al. |
| 4,835,256 A | 5/1989 | Taniguchi et al. |
| 4,845,196 A | 7/1989 | Cowling |
| 4,855,238 A | 8/1989 | Gray et al. |
| 4,897,471 A | 1/1990 | Stabinsky |
| 4,898,931 A | 2/1990 | Itoh et al. |
| 4,904,584 A | 2/1990 | Shaw |
| 4,921,698 A | 5/1990 | Shirai et al. |
| 4,925,793 A | 5/1990 | Goeddel et al. |
| 4,929,554 A | 5/1990 | Goeddel et al. |
| 4,944,941 A | 7/1990 | Ammann |
| 4,966,843 A | 10/1990 | McCormick et al. |
| 4,980,455 A | 12/1990 | Sakaguchi et al. |
| 5,004,689 A | 4/1991 | Fiers et al. |
| 5,041,376 A | 8/1991 | Gething et al. |
| 5,096,705 A | 3/1992 | Goeddel et al. |
| 5,109,120 A | 4/1992 | Ueno et al. |
| 5,157,004 A | 10/1992 | Sakaguchi et al. |
| 5,362,490 A | 11/1994 | Kurimoto et al. |
| 5,376,567 A | 12/1994 | McCormick et al. |
| 5,382,657 A | 1/1995 | Karasiewicz et al. |
| 5,518,899 A | 5/1996 | Kurimoto et al. |
| 5,541,293 A | 7/1996 | Stabinsky |
| 5,554,515 A | 9/1996 | Kurimoto et al. |
| 5,574,137 A | 11/1996 | Gray et al. |
| 5,582,824 A | 12/1996 | Goeddel et al. |
| 5,595,888 A | 1/1997 | Gray et al. |
| 5,661,009 A | 8/1997 | Stabinsky |
| 5,672,692 A | 9/1997 | Kurimoto et al. |
| 5,690,925 A | 11/1997 | Gray et al. |
| 5,711,944 A | 1/1998 | Gilbert et al. |
| 5,723,121 A | 3/1998 | Takenaga et al. |

(Continued)

FOREIGN PATENT DOCUMENTS

CA 2096532 5/1992

(Continued)

OTHER PUBLICATIONS

Arakawa, et al., *Role of Polycationic c-terminal Portion in the Structure and Activity of Recombinant Human Interferon-γ*, The Journal of Biological Chemistry, 261(18), Jun. 25, pp. 8534-8539 (1986).

(Continued)

*Primary Examiner*—Christine J. Saoud
*Assistant Examiner*—Jegatheesan Seharaseyon
(74) *Attorney, Agent, or Firm*—Donald J. Pochopien; Sharon M. Fujita; Norman J. Kruse

(57) ABSTRACT

A conjugate exhibiting interferon gamma activity and comprising at least one first non-polypeptide moiety covalently linked to an IFG polypeptide, the polypeptide comprising an amino acid sequence that differs from that of a parent IFNG polypeptide in at least one introduced and/or at least one removed amino acid residue comprising an attachment group for the non-polypeptide moiety. The conjugate may be used for treatment of various diseases.

15 Claims, No Drawings

U.S. PATENT DOCUMENTS

| | | | |
|---|---|---|---|
| 5,738,846 | A | 4/1998 | Greenwald et al. |
| 5,747,646 | A | 5/1998 | Hakimi et al. |
| 5,770,191 | A | 6/1998 | Johnson et al. |
| 5,792,834 | A | 8/1998 | Hakimi et al. |
| 6,042,822 | A | 3/2000 | Gilbert et al. |
| 6,046,034 | A | 4/2000 | Waschutza et al. |
| 6,120,762 | A | 9/2000 | Johnson et al. |
| 6,497,871 | B1 | 12/2002 | Gray et al. |

FOREIGN PATENT DOCUMENTS

| | | | |
|---|---|---|---|
| EP | 077 670 | B1 | 4/1983 |
| EP | 088 540 | A2 | 9/1983 |
| EP | 089 676 | A2 | 9/1983 |
| EP | 098 110 | A2 | 1/1984 |
| EP | 110 044 | A1 | 6/1984 |
| EP | 146 354 | A2 | 6/1985 |
| EP | 158 198 | A1 | 10/1985 |
| EP | 170 917 | B1 | 2/1986 |
| EP | 219 781 | A2 | 4/1987 |
| EP | 229 108 | B1 | 7/1987 |
| EP | 256 424 | B1 | 8/1987 |
| EP | 236 987 | B1 | 9/1987 |
| EP | 237 019 | A2 | 9/1987 |
| EP | 306 870 | A2 | 3/1989 |
| EP | 121 157 | B1 | 6/1989 |
| EP | 145 174 | B1 | 9/1989 |
| EP | 370 205 | A2 | 5/1990 |
| EP | 446 582 | B1 | 9/1991 |
| EP | 546 099 | B1 | 10/1994 |
| EP | 795 332 | A2 | 9/1997 |
| EP | 593 868 | B1 | 4/1998 |
| EP | 860 442 | A1 | 8/1998 |
| WO | 92/08737 | A1 | 11/1991 |
| WO | 92/22310 | A1 | 6/1992 |
| WO | 99/03887 | A1 | 7/1998 |
| WO | 99/67291 | A2 | 6/1999 |
| WO | 01-23006 | A1 | 9/2000 |
| WO | 01-36001 | A2 | 11/2000 |

OTHER PUBLICATIONS

Arakawa, et al., *Structure and Activity of Glycosylated Human Interferon-γ*, Journal of Interferon Research, 6:687-695 (1986).

Bulleid, et al., *Source of heterogeneity in secreted interferon-γ*, Biochem, J. 268:777-781 (1990).

Cantell, et al., *Differential Inactivation of Interferon by a Protease from Human Granulocytes*, Journal of Interferon Research 12:177-183 (1992).

Castro, et al., *The macroheterogeneity of recombinant human interferon-γ produced by Chinese-hamster ovary cells is affected by the protein and lipid content of the culture medium*, Biotechnol. Appl. Biochem., 21:87-100 (1995).

Curling, et al., *Recombinant human interferon-γ, Differences in glycosylation and proteolytic processing lead to heterogeneity in batch culture*, Biochem. J., 272:333-337 (1990).

Devos, et al., *Molecular cloning of human immune interferon cDNA and its expression in eukaryotic cells*, Nucleic Acids Research, 10(8), 2487-2501, Nov. 8, 1982.

Ealick, et al., *Three-Dimensional Structure of Recombinant Human Interferon-γ*, Science, 252:698-702 (1991).

Farrar, et al., *The Molecular Cell Biology of Interferon-γ and its Receptor*, Annu. Rev. Immunol. 11:572-611 (1993).

Gray, et al., *Structure of the human immune interferon gene*, Nature, 298:859-863 (Aug. 1992).

Griggs, et al., *The N-terminus and C-Terminus of IFN-γ Are Binding Domains for Cloned Soluble IFN-Y Receptor*, The Journal of Immunology, 149(2) 517-520 (Jul. 15, 1992).

Gu, et al., *Improvement of Interferon-γ Sialylation in Chinese Hamster Ovary Cell culture by Feeding of N-Acetylmannosamine*, Biotechnology & Bioengineering, 58(6) 642-648 (1998).

Haelewn, et al., *Interaction of truncated human interferon γ variants with the interferon γ receptor: crucial importance of Arg-129*, Biochem. J., 324, 591-595 (1997).

Harmon, et al., *Rapid Monitoring of Site-Specific Glycosylation Microheterogeneity of Recombinant Human Interferon-γ*, Anal. Chem., 68(9) 1465-1473 (1996).

Hogrefe, et al., *Amino Terminus Is Essential to the Structural Integrity of Recombinant Human Interferon-γ*, The Journal of Biological Chemistry, 264(21) 12179-86 (1989).

Hooker, et al., *Constraints on the Transport and Glycosylation of Recombinant IFN-γ in Chinese Hamster Ovary and Insect Cells*, Biotechnology & Bioengineering, 63(5) 559-572 (1999).

Hsu, et al., *Structure and activity of Recombinant Human Interferon-γ Analogs*, Journal of Interferon Research, 6:663-670 (1986).

James, et al., *N-Glycosylation of Recombinant Human Interferon-γ Produced in Different Animal Expression Systems*, Bio/Technology, 13:592-96 (Jun. 13, 1995).

Kita, et al., *Characterization of a Polyethylene Glycol Conjugate of Recombinant Human Interferon-γ*, Drug Design and Delivery, 6:157-167 (1990).

Kontsek, et al., *Engineered Acid-Stable Human Interferon Gamma*, Cytokine, 12(6) 708-710 (Jun. 2000).

Landar, et al., *Design, Characterization, and Structure of a Biologically Active Single-chain Mutant of Human IFN-γ*, J. Mol. Biol., 299:169-179 (2000).

Leinikki, et al., *Reduced Receptor Binding by a Human Interferon-γ Fragment Lacking 11 Carboxyl-Terminal Amino Acids*, Journal of Immunology, 139(10) 3360-3366 (1987).

Littman, et al., *Binding of Unglycosylated and Glycosylated Human Recombinant Interferon-γ to Cellular Receptors*, Journal of Interferon Research, 5: 471-476 (1985).

Lord, et al., *Functional Domains of Human Interferon Gamma Probed With Antipeptide Antibodies*, Molecular Immunology, 26(7) 637-640 (1989).

Luk, et al., *Structure-Function Analysis of the Human Interferon γ*, The Journal of Biological Chemistry, 265 (22) 13314-13319 (1990).

Lundell, et al., *Importance of the Loop connecting A and B Helices of Human Interferon-γ in Recognition by Interferon-γ Receptor**, The Journal of Biological Chemistry, 269(23) 16159-16162.

Lundell, et al., *Structural Elements Required for Receptor Recognition of Human Interferon-Gamma*, Pharmac. Ther. 64:1-21 (1994).

Lundell, et al., *The carboxyl-terminal region of human interferon γ is important for biological activity: mutagenic and NMR analysis*, Protein Engineering, 4(3) 335-341 (1991).

Lunn, et al., *A point mutation of human interferon γ abolishes receptor recognition*, Protein Engineering, 5(3) 253-257 (1992).

Lunn, et al., *A point mutation that decreases the thermal stability of human interferon γ*, Protein Engineering, 5(3) 249-252 (1992).

Mørtz, et al., *Mass spectrometric characterization of glycosylated interferon-γ variants separated by gel electrophoresis*, Electrophoresis, 17:926-931 (1996).

Nishi, et al., *Cloning and Expression of a Novel Variant of Human Interferon-γ cDNA*, J. Biochem, 97 (1) 153-159 (1985).

Nyberg, et al., *Metabolic Effects on Recombinant Interferon-γ Glycosylation in Continuous Culture of Chinese Hamster Ovary Cells*, Biotechnology & Bioengineering, 62(3) 336-347 (1999).

Oliver, et al., *The use of electrospray ionization MS to determine the structure of glycans in intact glycoproteins*, Biochem. Mass Spectro., 24:917-927 (1996).

Pan, et al., *Structural characterization of human interferon γ*, FEBS 145-149 (1987).

Rinderknecht, et al., *Natural Human Interferon-γ*, Journal of Biological Chemistry, 259(11) 6790-6797 (1984).

Riske, et al., *Characterization of Human Interferon-γ and Human Interleukin-2 from Recombinant Mammalian Cell Lines and Peripheral Blood Lymphocytes*, Lymphokine and Cytokine Research, 10 (3) 213-218, (1991).

Sakaguchi, et al., *Human interferon-γ lacking 23 COOH-terminal amino acids is biologically active*, FEBS Letters, 230(1,2) 201-204 (Mar. 1988).

Sano, et al., *Structural Characterization of Recombinant Human Interferon-Gammas Derived from Two Different Mammalian Cells*, Microbiol. Immunol., 32 (5) 499-510 (1988).

Sareneva, et al., *Biosynthesis and N-glycosylation of human interferon-γ Asn25 and Asn97 differ markedly in how efficiently they are glycosylated and in their oligosaccharide composition*, Eur. J. Biochem., 242:191-200 (1996).

Sareneva, et al., *N-glycosylation of human interferon-γ: glycans at Asn-25 are critical for protease resistance*, Biochem. J. 308:9-14 (1995).

Sareneva, et al., *Role of N-glycosylation in the synthesis, dimerization and secretion of human interferon-γ*, Biochem. J., 303:831-840 (1994).

Sareneva, et al., *Effect of Carbohydrates on the Pharmacokinetics of Human Interferon-γ*, Journal of Interferon Research, 13:267-269 (1993).

Seelig, et al., *Evidence for a Polypeptide Segment at the Carboxyl Terminus of Recombinant Human γ Interferon Involved in Expression of Biological Activity*, Biochemistry, 27(6) 1981-1987 (1988).

Slodowski, et al., *Carboxy-terminal truncated rhuIFN-γ with a substitution of Gln133 o Ser132 to leucine leads to higher biological activity than in the wild type*, Euro. J. Biochem, 202:1133-1140 (1991).

Subramaniam, et al., *The Carboxyl Terminus of Interferon-γ Contains a Functional Polybasic Nuclear Localization Sequence*, Journal of Biological Chemistry, 274(1) 403-407 (1999).

Tang, et al., *Studies on the PEGylation of Protein at a Specific Site: Sulfhydryl-PEGylation of 97 Cys-IFN-γ*, Acta Biochimica et Biophysica Sinica, 28(3) 1-5 (May 1996).

Taya, et al., *Cloning and structure of the human immune interferon-γ chromosomal gene*, The EMBO Journal, 1(8) 953-958 (1982).

Trousdale, et al., *Human Alpha and Gamma Interferon Analogs in Rabbits with Herpetic Keratitis*, Invest. Ophth. & Vis. Sci., 26(9) 1244-1251 (1985).

Waschütza, et al., *Interferon-γ variants with deletions in the AB surface loop*, Eur. J. Biochem., 256:303-309 (1998).

Wetzel, et al., *Mutations in Human Interferon Gamma Affecting Inclusion Body Formation Identified by a General Immunochemical Screen*, Bio/Technology, 9:731-737 (1991).

Zhang, et al., *Quantitative analysis and process monitoring of site-specific glycosylation microheterogeneity In recombinant human interferon-γ from Chinese hamster ovary cell culture by hydrophilic interaction chromatography*, Journal of Chromatogr. B, 712:73-82 (1998).

Ziesche, et al., *A Preliminary Study of Long-Term Treatment with Interferon Gamma-1b and Low-Dose Prednisolone in Patients with Idiopathic Pulmonary Fibrosis*, The New England Journal of Medicine, 341(7) 1264-1269 (1999).

Wetzel, et al., *Mutational Analysis of the C-terminus of Human Interferon-γ*, Protein Engineering, 3:(7) pp. 611-623(1990).

European Search Report for EP 00974356.8, Dec. 14, 2005.

MacDougall et al., Nov. 1999, J. Am. Soc. Nephrol, 10, 2392-2395.

Egrie et al., 1997, Blood 90, 56a.

Alberts, Mol. Biol. of the Cell, 2$^{nd}$ Ed., Garland Pub. NY, NY, (1989) at p. 446.

Tang et al., "Preparation of a New PEGylation reagent for Sulfhydryl-containing Polypeptide," Tet. Lett., 35:35, 6515-6516 (1994).

Tang et al., "Studies on the PEGylation of Protein at a Specific Site: Sulfhydryl-PEGylation of 97 Cys-IFN-y," Acta Biochimica et Biophysica Sinica, 28:3 312-315 (1996).

E38N INTERFERON GAMMA POLYPEPTIDE VARIANTS

This application is a continuation of U.S. Ser. No. 10/130,084, filed Sep. 04, 2002, now pending; which is a 371 of PCT/DK00/00631, filed Nov. 13, 2000; which claims the benefit of 60/166,293, filed Nov. 18, 1999 and also Denmark Patent Application No. 2000 00447, filed Mar. 17, 2000, as well as Denmark Patent Application No. 1999 01631, filed Nov. 12, 1999.

FIELD OF THE INVENTION

The present invention relates to conjugates with interferon-gamma-like activity, methods for their preparation, pharmaceutical compositions comprising the molecules and their use in the treatment of diseases.

BACKGROUND OF THE INVENTION

Interferon-gamma (IFNG) is a cytokine produced by T-lymphocytes and natural killer cells and exists as a homodimer of two noncovalently bound polypeptide subunits. The mature form of each dimer comprises 143 amino acid residues (shown in SEQ ID NO 2), the precursor form thereof including signal sequence of 166 amino acid residues (shown in SEQ ID NO 1).

Each subunit has two potential N-glycosylation sites (Aggarwal et al., Human Cytokines, Blackwell Scientific Publications, 1992) at positions 25 and 97. Depending on the degree of glycosylation the molecular weight of IFNG in dimer form is 34–50 kDa (Farrar et al., Ann. Rev. Immunol, 1993, 11:571–611).

The primary sequence of wildtype human IFNG (huIFNG) was reported by Gray et al. Nature 298:859–863, 1982), Taya et al. (EMBO J. 1:953–958, 1982), Devos et al. (Nucleic Acids Res. 10:2487–2501, 1982) and Rinderknecht et al. (J. Biol. Chem. 259:6790–6797, 1984), and in EP 77670, EP 89676 and EP 110044. The 3D structure of huIFNG was reported by Ealick et al. (Science 252:698–702, 1991).

Various naturally-occurring or mutated forms of the IFNG subunit polypeptides have been reported, including one comprising a Cys-Tyr-Cys N-terminal amino acid sequence (positions (−3)–(−1) relative to SEQ ID NO 2), one comprising an N-terminal methionine (position −1 relative to SEQ ID NO 2), and various C-terminally truncated forms comprising 127–134 amino acid residues. It is known that 1–15 amino acid residues may be deleted from the C-terminus without abolishing IFNG activity of the molecule. Furthermore, heterogeneity of the huIFNG C-terminus was described by Pan et al. (Eur. J. Biochem. 166:145–149, 1987).

huIFNG muteins were reported by Slodowski et al. (Eur. J. Biochem. 202 :1133–1140, 1991), Luk et al. (J. Biol. Chem. 265:13314–13319, 1990), Seelig et al., (Biochemistry 27:1981–1987, 1988), Trousdale et al. (Invest. Ophthalmol. Vis. Sci. 26:1244–1251, 1985), and in EP 146354. A natural huIFNG variant was reported by Nishi et al. (J. Biochem. 97:153–159, 1985).

U.S. Pat. No. 6,046,034 discloses thermostable recombinant huIFNG (rhuIFNG) variants having incorporated up to 4 pairs of cysteine residues to enable disulphide bridge formation and thus stabilization of the IFNG variant in homodimer form.

WO 92/08737 discloses IFNG variants comprising an added methionine in the N-terminal end of the full (residues 1–143) or partial (residues 1–132) amino acid sequence of wildtype human IFNG. EP 219 781 discloses partial huIFNG sequences comprising amino acid residues 3–124 (of SEQ ID NO 2). U.S. Pat. No. 4,832,959 discloses partial huIFNG sequences comprising residues 1–127, 5–146 and 5–127 of an amino acid sequence that compared to SEQ ID NO 2 has three additional N-terminal amino acid residues (CYC). U.S. Pat. No. 5,004,689 discloses a DNA sequence encoding huIFNG without the 3 N-terminal amino acid residues CYC and its expression in E. coli. EP 446382 discloses E. coli produced rhuIFNG free of an N-terminal methionine. U.S. Pat. No. 6,120,762 discloses a peptide fragment of huIFNG comprising residues 95–134 thereof (relative to SEQ ID NO 2).

High level expression of rhuIFNG was reported by Wan et al. (Sci. Sin. B 24:1076–1084, 1994).

Glycosylation variation in rhuIFNG has been reported by Curling et al. (Biochem. J. 272:333–337, 1990) and Hooker et al., (J. of Interferon and Cytokine Research, 1998, 18: 287–295).

Polymer-modification of rhuIFNG was reported by Kita et al. (Drug Des. Deliv. 6:157–167, 1990), and in EP 236987 and U.S. Pat. No. 5,109,120.

WO 92/22310 discloses asialoglycoprotein conjugate derivatives of interferons, inter alia huIFNG.

IFNG fusion proteins have been described. For instance, EP 237019 discloses a single chain polypeptide having region exhibiting interferon β activity and one region exhibiting IFNG activity.

EP 158 198 discloses a single chain polypeptide having a region exhibiting IFNG activity and a region exhibiting IL-2 activity. Several references described single chain dimeric IFNG proteins, e.g. Landar et al. (J. Mol. Biol., 2000, 299:169–179).

WO 99/02710 discloses single chain polypeptides, one example among many being IFNG.

WO 99/03887 discloses PEGylated variants of polypeptides belonging to the growth hormone superfamily, wherein a non-essential amino acid residue located in a specified region of the polypeptide has been replaced by a cysteine residue. IFNG is mentioned as one example of a member of the growth hormone super family, but modification thereof is not discussed in any detail.

IFNG has been suggested for treatment of interstitial lung diseases (also known as Interstitial Pulmonary Fibrosis (IPF)) (Ziesche et al. (N. Engl. J. Med. 341:1264–1269, 1999 and Chest 110:Suppl:25S, 1996) and EP 795332) for which purpose IFNG can be used in combination with prednisolone. In addition to IPF, granulomatous diseases (Bolinger et al, Clinical Pharmacy, 1992, 11:834–850), certain mycobacterial infections (N. Engl. J. Med. 330:1348–1355, 1994), kidney cancer (J. Urol. 152:841–845, 1994), osteopetmsis (N. Engl. J. Med. 332:1594–1599, 1995), scleroderma (J. Rheumatol. 23:654–658, 1996), hepatitis B (Hepatogastroenterology 45:2282–2294, 1998), hepatitis C (Int. Hepatol. Communic. 6:264–273, 1997), septic shock (Nature Medicine 3:678–681, 1997), and rheumatoid arthritis may be treated with IFNG.

As a pharmaceutical compound rhuIFNG is used with a certain success, above all, against some viral infections and tumors. rhuIFNG is usually applicable via parenteral, preferably via subcutaneous, injection. Maximum serum concentrations have been found after seven hours, half life in plasma is 30 minutes after iv administration. For this reason efficient treatment with rhuIFNG involves frequent injections. The main adverse effects consist of fever, chills, sweating, headache, myalgia and drowsiness. These effects are associated with injecting rhuIFNG and are observed within the first hours after injection. Rare side effects are local pain and erythema, elevation of liver enzymes, reversible granulo- and thrombopenia and cardiotoxicity.

It is desirable to provide novel molecules with IFNG-activity which have improved properties in terms of pharmacokinetics, homogeneity, immunogenicity and other adverse side-effects as compared with huIFNG or rhuIFNG.

BRIEF DISCLOSURE OF THE INVENTION

This application discloses improved IFNG-like molecules providing one or more of the aforementioned desired benefits. In a first aspect the invention relates to a conjugate exhibiting IFNG activity and comprising at least one first non-polypeptide moiety covalently attached to an IFNG polypeptide, the polypeptide comprising an amino acid sequence that differs from that of a parent IFNG polypeptide in at least one introduced and/or at least one removed amino acid residue comprising an attachment group for the non-polypeptide moiety. The conjugates have extended in vivo half-life as compared to huIFNG and rhuIFNG and optionally causes a reduced immune response as compared to rhuIFNG. Optionally, the class of molecules also has further improved properties in terms of producability of homogenous molecules, improved stability towards proteolysis and/or increased bioavailability.

Consequently, the conjugate of the invention offers a number of advantages over the currently available IFNG compounds, including longer duration between injections or other forms of administration, fewer side effects, and/or increased efficiency due to reduction in antibodies. Moreover, higher doses of active protein and thus a more effective therapeutic response may be obtained by use of a conjugate of the invention.

In a further aspect the invention relates to a conjugate exhibiting IFNG activity comprising at least one N-terminally PEGylated IFNG polypeptide. The IFNG polypeptide may be huIFNG or any of the IFNG polypeptides described herein.

In still further aspects the invention relates to means and methods for preparing a conjugate of the invention, including nucleotide sequences and expression vectors as well as methods for preparing the polypeptide or the conjugate.

In yet further aspects the invention relates to a therapeutic composition comprising a conjugate of the invention, to a conjugate or composition of the invention for use in therapy, to the use of a conjugate or composition in therapy or for the manufacture of a medicament for treatment of diseases.

Finally, the invention relates to the use of specified IFNG conjugates for the manufacture of a medicament, a pharmaceutical composition or a kit-of-parts for the treatment of interstitial lung diseases, cancer, infections and/or inflammatory diseases, and in the case of interstitial lung diseases, optionally, furthermore in combination with glucocorticoids.

DETAILED DESCRIPTION OF THE INVENTION

Definitions

In the context of the present application and invention the following definitions apply:

The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties. The term covalent attachment means that the polypeptide and the non-polypeptide moiety are either directly covalently joined to one another, or else are indirectly covalently joined to one another through an intervening moiety or moieties, such as a bridge, spacer, or linkage moiety or moieties. Preferably, the conjugate is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used about the polypeptide part of the conjugate.

The term "non-polypeptide moiety" is intended to indicate a molecule that is capable of conjugating to an attachment group of the IFNG polypeptide. Preferred examples of such molecule include polymer molecules, lipophilic compounds, sugar moieties or organic derivatizing agents. When used in the context of a conjugate of the invention it will be understood that the non-polypeptide moiety is linked to the polypeptide part of the conjugate through an attachment group of the polypeptide.

The term "polymer molecule" is defined as a molecule formed by covalent linkage of two or more monomers, wherein none of the monomers is an amino acid residue, except where the polymer is human albumin or another abundant plasma protein. The term "polymer" may be used interchangeably with the term "polymer molecule". The term "sugar moiety" is intended to indicate a carbohydrate molecule attached by in vivo or in vitro glycosylation, such as N- or O-glycosylation. Except where the number of non-polypeptide moieties, such as polymer molecule(s), in the conjugate is expressly indicated every reference to "a non-polypeptide moiety" contained in a conjugate or otherwise used in the present invention shall be a reference to one or more non-polypeptide moieties in the conjugate.

The term "attachment group" is intended to indicate an amino acid residue group capable of coupling to the relevant non-polypeptide moiety such as a polymer molecule or a sugar moiety. Useful attachment groups and their matching non-polypeptide moieties are apparent from the table below.

| Attachment group | Amino acid | Examples of non-polypeptide moiety | Conjugation method/Activated PEG | Reference |
|---|---|---|---|---|
| —NH$_2$ | N-terminal, Lys | Polymer, e.g. PEG | mPEG-SPA Tresylated mPEG | Shearwater Inc. Delgaod et al, critical reviews in Therapeutic |

-continued

| Attachment group | Amino acid | Examples of non-polypeptide moiety | Conjugation method/Activated PEG | Reference |
|---|---|---|---|---|
| —COOH | C-term, Asp, Glu | Polymer, e.g. PEG Sugar moiety | mPEG-Hz In vitro coupling | Drug Carrier Systems 9(3,4):249–304 (1992) Shearwater Inc |
| —SH | Cys | Polymer, e.g. PEG, Sugar moiety | PEG-vinylsulphone PEG-maleimide In vitro coupling | Shearwater Inc Delagoda et al, critical reviews in Therapeutic Drug Carrier Systems 9(3,4):249–304 (1992) |
| —OH | Ser, Thr, OH—, Lys | Sugar moiety | In vivo O-linked glycosylation | |
| —CONH$_2$ | Asn as part of an N-glycosylation site | Sugar moiety | In vivo glycosylation | |
| Aromatic residue | Phe, Tyr, Trp | Sugar moiety | In vitro coupling | |
| —CONH$_2$ | Gln | Sugar moiety | In vitro coupling | Yan and Wold, Biochemistry, 1984, Jul 31; 23(16):3759–65 |
| Aldehyde Ketone | Oxidized carbohydrate | Polymer, e.g. PEG, PEG-hydrazide | PEGylation | Andresz et al., 1978, Makromol, Chem. 179:301; WO 92/16555, WO 00/23114 |
| Guanidino | Arg | Sugar moiety | In vitro coupling | Lundblad and Noyes, Chimical Reagents for Protein Modification, CRC Press Inc. Boca Raton, Fl |
| Imidazole ring | His | Sugar moiety | In vitro coupling | As for guanidine |

For in vivo N-glycosylation, the term "attachment group" is used in an unconventional way to indicate the amino acid residues constituting an N-glycosylation site (with the sequence N-X'-S/T/C-X", wherein X' is any amino acid residue except proline, X" any amino acid residue that may or may not be identical to X' and that preferably is different from proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the parent polypeptide is to be understood as one, two or all of the amino acid residues constituting an N-glycosylation site is/are to be altered in such a manner that either a functional N-glycosylation site is introduced into the amino acid sequence or removed from said sequence.

In the present application, amino acid names and atom names (e.g. CA, CB, CD, CG, SG, NZ, N, O, C, etc.) are used as defined by the Protein DataBank (PDB) (see the pdb.org website) which are based on the IUPAC nomenclature (IUPAC Nomenclature and Symbolism for Amino Acids and Peptides (residue names, atom names etc.), Eur. J. Biochem., 138, 9–(1984) together with their corrections in Eur. J. Biochem., 152, 1 (1985). CA is sometimes referred to as Cα, CB as Cβ. The term "amino acid residue" is intended to indicate an amino acid residue contained in the group consisting of alanine (Ala or A), cysteine (Cys or C), aspartic acid (Asp or D), giutamic acid (Glu or E), phenylalanine (Phe or F), glycine (Gly or G), histidine (His or H), isoleucine (Ile or I), lysine (Lys or K), leucine (Leu or L), methionine (Met or M), asparagines (Asn or N), proline (Pro or P), glutamine (Gln or Q), arginine (Arg or R), serine (Ser or S), threonine (Thr or T), valine (Val or V), tryptophan (Trp or W) and tyrosine (Tyr or Y) residues. The numbering of amino acid residues in this document is from the N-terminus of huIFNG without signal peptide (i.e. SEQ ID NO 2). The terminology used for identifying amino acid positions/substitutions is illustrated as follows N25 (indicates residue position #25 is occupied by asparagine in the amino acid sequence shown in SEQ ID NO 2), N25C (indicates that the Asp residue of position 25 has been replaced with a Cys residue). Multiple substitutions are indicated with a "+", e.g. Q1N+P3T/S means an amino acid sequence which comprises a substitution of the Gln residue in position 1 with an Asn residue and a substitution of the Pro residue in position 3 with a Thr or Ser residue, preferably a Thr residue.

The term "nucleotide sequence" is intended to indicate a consecutive stretch of two or more nucleotide molecules.

The nucleotide sequence may be of genomic, cDNA, RNA, semisynthetic, synthetic origin, or any combinations thereof.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "introduce" is primarily intended to mean substitution of an existing amino acid residue, but may also mean insertion of an additional amino acid residue. The term "remove" is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "one difference" or "differs" as used about the amino acid sequence of an IFNG polypeptide described herein is intended to allow for additional differences being present. Accordingly, in addition to the specified amino acid difference, other amino acid residues than those specified may be mutated.

The term "functional in vivo half-life" is used in its normal meaning, i.e. the time in which 50% of conjugate molecules circulate in the plasma or bloodstream prior to being cleared (also termed "serum half-life"), or the time in which 50% of a given functionality of the conjugate is retained. The polypeptide or conjugate is normally cleared by the action of one or more of the reticuloendothelial systems (RES), kidney, spleen or liver, or by specific or unspecific proteolysis. Normally, clearance depends on size (relative to the cutoff for glomerular filtration), charge, attached carbohydrate chains, and the presence of cellular receptors for the protein. The functionality to be retained is normally selected from antiviral, antiproliferative, immunomodulatory or IFNG receptor binding activity. The functional in vivo half-life may be determined by any suitable method known in the art as further discussed in the Methods section hereinafter.

The term "increased functional in vivo half-life" is used to indicate that the functional in vivo half-life of the conjugate is statistically significant increased relative to that of a reference molecule, such as huIFNG, optionally in glycosylated form, e.g. non-conjugated huIFNG or rhuIFNG as determined under comparable conditions.

The term "immunogenicity" as used in connection with a given substance is intended to indicate the ability of the substance to induce a response from the human immune system. The immune response may be a cell or antibody mediated response (see, e.g., Roitt: Essential Immunology ($8^{th}$ Edition, Blackwell) for further definition of immunogenicity).

The term "reduced immunogenicity" is intended to indicate that the conjugate of the present invention, gives rise to a measurably lower immune response than a reference molecule, such as huIFNG or rhuIFNG as determined under comparable conditions.

The term "exibiting IFNG activity" is intended to indicate that the polypeptide has one or more of the functions of native IFNG, in particular huIFNG or rhuIFNG, including the capability to bind to an IFNG receptor and cause transduction of the signal transduced upon huIFNG-binding of its receptor as determined in vitro or in viva (i.e. in vitro or in vivo bioactivity). The IFNG receptor has been described by Aguet et al (Cell 55:273–280, 1988) and Calderon et al. (Proc. Natl. Acad. Sci. USA 85:4837–4841, 1988). The "IFNG polypeptide" is a polypeptide exhibiting IFNG activity, and is used herein about the polypeptide in monomer or dimeric form, as appropriate. For instance, when specific substitutions are indicated these are normally indicated relative to the IFNG polypeptide monomer. When reference is made to the IFNG part of a conjugate of the invention this is normally in dimeric form (and thus, e.g., comprises two IFNG polypeptide monomers modified as described). The dimeric form of the IFNG polypeptides may be provided by the normal association of two monomers or be in the form of a single chain dimeric IFNG polypeptide.

The IFNG polypeptide described herein may have an in vivo or in vitro bioactivity of the same magnitude as huIFNG or rhuIFNG or lower or higher, e.g. an in viva or in vitro bioactivity of 1–100% of that of huIFNG or rhuIFNG, as measured under the same conditions, e.g. 1–25% or 1–50% or 25–100% or 50–100% of that of huIFNG or rhuIFNG.

The term "parent IFNG" is intended to indicate the molecule to be modified in accordance with the present invention. Normally, the parent IFNG is encoded by a nucleotide sequence, which is modified in accordance with the present invention so as to encode the polypeptide part of a conjugate of the invention. The parent IFNG is normally huIFNG or rhuIFNG or a variant or fragment thereof. A "variant" is a polypeptide, which differs in one or more amino acid residues: from its parent polypeptide, normally in 1, 2, 3, 4, 5, 6, 7, 8, 9, 10, 11, 12, 13, 14 or 15 amino acid residues. A fragment is a part of the full-length huIFNG sequence exhibiting IFNG activity, e.g. a C-terminally or N-terminally truncated version thereof.

The term "functional site" is intended to indicate one or more amino acid residues which is/are essential for or otherwise involved in the function or performance of IFNG. Such amino acid residues are "located at" the functional site. The functional site may be determined by methods known in the art and is preferably identified by analysis of a structure of the polypeptide complexed to a relevant receptor, such as the IFNG receptor.

Conjugate of the Invention

As stated above, in a first aspect the invention relates to conjugate exhibiting IFNG activity and comprising at least one first non-polypeptide moiety covalently attached to an IFNG polypeptide, the polypeptide comprising an amino acid sequence that differs from that of a parent IFNG polypeptide in at least one introduced and/or at least one removed amino acid residue comprising an attachment group for the non-polypeptide moiety.

By removing or introducing an amino acid residue comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the IFNG polypeptide) and thereby obtain a new conjugate molecule, which exhibits IFNG activity and in addition one or more improved properties as compared to huIFNG or rhuIFNG based molecules available today. For instance, by introduction of attachment groups, the IFNG polypeptide is boosted or otherwise altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation or reduced IFNG activity of the resulting conjugate due to impaired receptor recognition). Further, it may be advantageous to remove an attachment group located closely to another attachment group in order to avoid heterogeneous conjugation to such groups. In preferred embodiments more than one amino acid residue of the IFNG polypeptide is altered, e.g. the alteration embraces removal as well as introduction of amino acid residues comprising attachment sites for the non-polypeptide moiety of choice. This embodiment is considered of particular interest in that it is possible to specifically design the IFNG polypeptide-so as to obtain an optimal conjugation to the non-polypeptide moiety.

In addition to the removal and/or introduction of amino acid residues the polypeptide may comprise other substitutions that are not related to introduction and/or removal of amino acid residues comprising an attachment group for the non-polypeptide moiety.

While the parent polypeptide to be modified by the present invention can be any polypeptide with IFNG activity, and thus be derived from any origin, e.g. a non-human mammalian origin, it is preferred that the parent polypeptide is huIFNG with the amino acid sequence shown in SEQ ID NO 2 or a variant or fragment thereof. Examples of variants of hIFNG are described in the background of the invention above, and include, e.g. huIFNG with the N-terminal addition CYC and the cysteine modified variants described in U.S. Pat. No. 6,046,034. Specific examples of fragments are those disclosed in the Background of the Invention section above and include huIFNG C-terminally truncated with 1–15 amino acid residues, e.g. with 1, 2, 3, 4, 5, 6, 7, 8, 9, 10, 11, 12, 13, 14, or 15 amino acid residues, and/or N-terminally truncated with 1–3 amino acid residues.

It will be understood that when the parent IFNG polypeptide, is a variant or fragment of huIFNG, the modified IFNG polypeptide prepared from such parent comprises the mutations or truncations of the parent.

Also, the parent IFNG polypeptide can be a hybrid molecule between an IFNG polypeptide monomer and another homologous polypeptide optionally containing one or more additional substitutions introduced into the hybrid molecule. Such hybrids, are described in the Background of the Invention section above. Such a hybrid molecule may contain an amino acid sequence, which differs in more than 15 such as more than 10 amino acid residues from the amino acid sequence shown in SEQ ID NO 2. In order to be useful in the present invention the hybrid molecule exhibits IFNG activity.

Non-human parent IFNG's can be modified analogously to what is described herein, e.g. by modifying a corresponding position of the non-human parent IFNG (e.g. as determined from an alignment of the amino acid sequence or 3D structure of said IFNG with huIFNG) to the position described herein.

It will be understood that the amino acid residue comprising an attachment group for an non-polypeptide moiety, either it be removed or introduced, is selected on the basis of the nature of the non-polypeptide moiety part of choice and, in most instances, on the basis of the conjugation method to be used. For instance, when the non-polypeptide moiety is a polymer molecule such as a polyethylene glycol or polyalkylene oxide derived molecule amino acid residues capable of functioning as an attachment group may be selected from the group consisting of cysteine, lysine aspartic acid, glutamic acid and arginine. When the non-polypeptide moiety is a sugar moiety the attachment group is, e.g. an in vivo glycosylation site, preferably an N-glycosylation site.

Whenever an attachment group for a non-polypeptide moiety is to be introduced into or removed from the IFNG polypeptide in accordance with the present invention, the position of the polypeptide to be modified is conveniently selected as follows:

The position is preferably located at the surface of the IFNG polypeptide, and more preferably occupied by an amino acid residue that has more than 25% of its side chain exposed to the solvent, preferably more than 50% of its side chain exposed to the solvent, as determined on the basis of a 3D structure or model of IFNG in its dimeric form, the structure or model optionally further comprising one or two IFNG receptor molecules. Such positions (e.g. representing more than 25% or more than 50% surface exposure in model without or with receptor molecules) are listed in the Materials and Methods section herein.

Also of interest is to modify any of the 23 C-terminal amino acid residues of the parent BEG (by introduction and/or removal of amino acid residues comprising an attachment group for the non-polypeptide moiety) since such residues are believed to be located at the surface of the IFNG polypeptide.

Furthermore, in the IFNG polypeptide part of a conjugate of the invention attachment groups located at the receptor-binding site of IFNG has preferably been removed, preferably by substitution of the amino acid residue comprising such group. Amino acid residues of the IFNG receptor-binding site are identified in the Materials and Methods section below. In the case of a single chain IFNG polypeptide it may be sufficient to remove attachment groups in the receptor-binding site of only one of the monomers and thereby obtain a single chain IFNG polypeptide conjugate with one active and one inactive receptor-binding site.

In order to determine an optimal distribution of attachment groups, the distance between amino acid residues located at the surface of the IFNG polypeptide is calculated on the basis of a 3D structure of the IFNG dimeric polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the IFNG polypeptide part of a conjugate of the invention, any of said distances is preferably more than 8 Å, in particular more than 10 Å in order to avoid or reduce heterogeneous conjugation.

Also, the amino acid sequence of the IFNG polypeptide may differ from that of a parent IFNG polypeptide in that one or more amino acid residues constituting part of an epitope has been removed, preferably by substitution to an amino acid residue comprising an attachment group for the non-polypeptide moiety, so as to destroyed or inactivate the epitope. Epitopes of huIFNG or rhuIFNG may be identified by use of methods known in the art, also known as epitope mapping, see, e.g. Romagnoli et al., Biol Chem, 1999, 380(5):553–9, DeLisser H M, Methods Mol Biol, 1999, 96:11–20, Van de Water et al., Clin Immunol Immunopathol, 1997, 85(3):229–35, Saint-Remy J M, Toxicology, 1997, 119(1):77–81, and Lane D P and Stephen C W, Curr Opin Immunol, 1993, 5(2):268–71. One method is to establish a phage display library expressing random oligopeptides of e.g. 9 amino acid residues. IgG1 antibodies from specific antisera towards huIFNG or rhuIFNG are purified by immunoprecipitation and the reactive phages are identified by immunoblotting. By sequencing the DNA of the purified reactive phages, the sequence of the oligopeptide can be determined followed by localization of the sequence on the 3D-structure of the IFNG. The thereby identified region on the structure constitutes an epitope that then can be selected as a target region for introduction of an attachment group for the non-polypeptide moiety.

In order to avoid too much disruption of the structure and function of the parent IFNG molecule the total number of amino acid residues to be altered in accordance with the present invention (as compared to the amino acid sequence shown in SEQ ID NO 2) typically does not exceed 15. Preferably, the IFNG polypeptide comprises an amino acid sequence, which differs in 1–15 amino acid residues from the amino acid sequence shown in SEQ ID NO 2, such as in 1–8 or 2–8 amino acid residues, e.g. in 1–5 or 2–5 amino acid residue from the amino acid sequence shown in SEQ ID NO 2. Thus, normally the IFNG polypeptide comprises an amino acid sequence which differs from the mature part of the amino acid sequence shown in SEQ ID NO 2 in 1, 2, 3, 4, 5, 6, 7, 8, 9, 10, 11, 12, 13, 14 or 15 amino acid residues. Preferably, the above numbers represent either the total number of introduced or the total number of removed amino acid residues comprising an attachment group for the relevant non-polypeptide moiety/ies, or the total number of introduced and removed amino acid residues comprising such group.

The exact number of attachment groups available for conjugation and present in the IFNG polypeptide in dimeric form is dependent on the effect desired to be achieved by the conjugation. The effect to be obtained is, e.g. dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.).

The IFNG polypeptide part of a conjugate of the invention may be in truncated form (e.g. truncated in 1–15 C-terminal amino acid residues as described further above in connection with the parent IFNG polypeptide, or truncated in 1–3 N-terminal amino acid residues.

Functional in vivo half-life is e.g. dependent on the molecular weight of the conjugate and the number of attachment groups needed for providing increased half-life thus depends on the molecular weight of the non-polypeptide moiety in question. In one embodiment, the conjugate of the invention has a molecular weight of at least 67 kDa, in particular at least 70 kDa as measured by SDS-PAGE according to Laemmli, U. K., Nature Vol 227 (1970), p680–85. IFNG has a Mw in the range of about 34–50 kDa, and therefore additional about 20–40 kDa is required to obtain the desired effect. This may be, e.g., be provided by 2–4 10 kDa PEG molecules or as otherwise described herein.

In the conjugate of the invention it is preferred that at least about 50% of all conjugatable attachment groups, such as at least 80% and preferably all of such groups are occupied by the relevant non-polypeptide moiety. Accordingly, in a preferred embodiment the conjugate of the invention comprises, e.g., 1–10 non-polypeptide moieties, such as 2–8 or 3–6.

As mentioned above under physiological conditions IFNG exists as a dimeric polypeptide. In accordance with the invention the IFNG polypeptide part of a conjugate of the invention is normally in homodimeric form (e.g. prepared by association of two IFNG polypeptide molecules prepared as described herein). However, if desired the IFNG polypeptide part of a conjugate of the invention may be provided in single chain form, wherein two IFNG polypeptide monomers are, linked via a peptide bond or a peptide linker. Providing the IFNG polypeptide in single chain form has the advantage that the two constituent IFNG polypeptides may be different which can be advantageous, e.g., to enable asymmetric mutagenesis of the polypeptides. For instance, PEGylation sites can be removed from the receptor-binding site from one of the monomers, but retained in the other. Thereby, after PEGylation one monomer has an intact receptor-binding site, whereas the other may be fully PEGylated (and thus provide significantly increased molecular weight.

Preferably, the conjugate of the invention has one or more of the following improved properties: 1) Increased functional in vivo half-life as compared to huIFNG or rhuIFNG, e.g. an increase of about at least 5-fold, such as at least 10-fold or even higher. 2) Reduced immunogenicity as compared to huIFNG or rhuIFNG, e.g. a reduction of at least 25%, such as at least 50%, and more-preferably at least 75%.

Conjugate of the Invention wherein the Non-polypeptide Moiety is a Sugar Moiety

In a preferred embodiment of a conjugate of the invention the first non-polypeptide moiety is a sugar moiety, e.g. an O-linked or N-linked sugar moiety, and the IFNG polypeptide comprises at least, one removed and/or at least one introduced in vivo glycosylation site.

For instance, an in viva glycosylation site is introduced into a position of the parent IFNG polypeptide occupied by an amino acid residue exposed to the surface of the polypeptide, preferably with more than 25% of the side chain exposed to the solvent, in particular more than 50% exposed to the solvent (these positions are identified in the Methods section herein). The N-glycosylation site is introduced in such a way that the N-residue of said site is located in said position. Analogously, an O-glycosylation site is introduced so that the S or T residue making up such site is located in said position. Furthermore, in order to ensure efficient glycosylation it is preferred that the in vivo glycosylation site, in particular the N residue of the N-glycosylation site or the S or T residue of the O-glycosylation site, is located within the 118 N-terminal amino acid residues of the IFNG polypeptide, more preferably within the 93 N-terminal amino acid residues. Still more preferably, the in vivo glycosylation site is introduced into a position wherein only one mutation is required to create the site (i.e. where any other amino acid residues required for creating a functional glycosylation site is already present in the molecule).

For instance, substitutions that lead to introduction of an additional N-glycosylation site at positions exposed at the surface of the IFNG polypeptide and occupied by amino acid residues having more than 25% of the side chain exposed to the surface (in a structure with receptor molecule) include:

Q1N+P3S/T, P3N+V5S/T, K6N+A8S/T, E9N+L11S/T, K12S/T, K13N+F15S/T, Y14N+N16S/T, G18S/T, G18N, G18N+S20T, H19N+D21S/T, D21N+A23S/T, G26N+L28S/T, G31N+L33S/T, K34N+W36S/T, K37S/T, K37N+E39S/T, E38 N, E38N+S40T, E39N+D41S/T, S40N+R42S/T, K55N+F57S/T, K58N+F60S/T, K61S/T, K61N+D63S/T, D62N+Q64S/T, D63N, D63N+S65T, Q64N+I66S/T, S65N+Q67S/T, Q67N, Q67N+S69T, K68N+V70S/T, E71N+I73S/T, T72N+K74S/T, K74N+D76S/T, E75N+M77S/T, K80S/T, V79N+F81S/T, K80N+F82S/T, N85S/T, S84N+K86S/T, K87S/T, K86N+K88S/T, K87N+R89S/T, D90N+F92S/T, E93N+L95S/T, K94N, K94N+T96S, S99N, S99N+T101S, T101N+L103S/T, D102N+N104S/T, L103N+V105S/T, Q106S/T, E119N, E119N+S121T, P122N+A124S/T, A123N+K125S/T, A124N, A124N+T126S, K125N+G127S/T, T126N+K128S/T, G127N+R129S/T, K129N+K130S/T, R129N+R131S/T, K130N, K130N+S132T, R113N+Q133S/T, S132N+M134S/T, Q133N+L135S/T, M134N+F136S/T, L135N+R137S/T, F136N+G138S/T, R137N+R139S/T, G138N+R140S/T, R139N+A141S/T, R140N and R140N+S142T, the substitution being indicated relative to huIFNG with the amino acid sequence shown in SEQ ID NO 2. S/T indicates a substitution to a serine or threonine residue, preferably a threonine residue.

Substitutions that lead to introduction of an additional N-glycosylation site at positions exposed at the surface of the IFNG polypeptide having more than 50% of the side chain exposed to the surface (in a structure with receptor molecule) include:

P3N+V5S/T, K6N+A8S/T, K12S/T, K13N+F15S/T, G18S/T, D21N+A23S/T, G26N+T28S/T, G31+L33S/T, K34N+W36S/T, K37N+E39S/T, E38N, E38N+S40S/T E39N+41S/T, K35+F57S/T, K58N+F60S, K61S/T, D62N+Q64S/T, Q64N+I66S/T, S65N+Q67S/T, K68N+V70S/T, E71N+I73S/T, E75N+M77S/T, N85S/T, S84N+K86S/T, K86N+K88S/T, K87N+R89S/T, K94N, K94N+T96S, S99N, S99N+T101S, T101N+L103S/T, D102N+N104S/T, L103N+V105S/T, Q106S/T, P122N+A124S/T A123N+K125S/T, A124N, A124N+T126S, K125N+G127S/T, T126N+K128S/T, G127N+R129S/T, K128N+K130S/T, R129N+R131S/T, K130N, K130N+S132T, R131N+Q133S/T, S132+M134S/T, Q133N+L135S/T, M134N+F136S/T, L135N+R137S/T, F136N+G138S/T, R137N+R139S/T, G138N+R140S/T, R139N+A141S/T, R140N and R140N+S142T, the substitution being indicated-relative to huIFNG with the amino acid sequence shown in SEQ ID NO 2.

Substitutions where only one amino acid mutation is required to introduce an N-glycosylation site include K12S/T, G18S/T, G18N, K37S/T, E38N, M45N, I49N, K61S/T, D63 N, Q67N, V70N, K80S/T, F82N, N85S/T, K87S/T, K94N, S99N, Q106S/T, E119N, A124N, K130N and R140N, in particular K12S/T, G18N, G18S/T, K37S/T, E38N, K61S/T, D63N, Q67N, K80S/T, N85S/T, K94N, S99N, Q106S/T, A124N, K130N, and R140N (positions with more than 25% of its site chain exposed to the surface (in a structure without receptor molecule), or more preferably G18N, E38N, D63N, Q67N, K94N, S99N, A124N, K130N and R140N (with more than 50% of its side chain exposed to the surface in a structure without receptor molecule).

From the above lists of substitutions, it is preferable to select substitutions located within the 118 N-terminal amino acid residues, in particular within the 93 N-terminal amino acid residues.

As indicated above, in addition to one or more introduced glycosylation sites, existing glycosylation sites may have been removed from the IFNG polypeptide. For instance, any of the above listed substitutions to introduce a glycosylation site may be combined with a substitution to remove any of the two natural N-glycosylation sites of huIFNG. For instance, the IFNG polypeptide may comprise a substitution of N25 and/or N97, e.g. one of the substitutions N25K/C/D/E and/or N97K/C/D/E, if the conjugate of the invention comprises a non-polypeptide polypeptide having the relevant of K, C, D, E as an attachment group.

The IFNG polypeptide part of a conjugate of the invention may contain a single in vivo glycosylation site pr monomer. However, in order to become of a sufficient size to increase functional in vivo half-life it is often desirable that the polypeptide comprises more than one in vivo glycosylation site, in particular 2–7 in vivo glycosylation sites, such as 2, 3, 4, 5, 6 or 7 in vivo glycosylation sites. Thus, the IFNG polypeptide may comprise one additional glycosylation site pr monomer, or may comprise two, three, four, five, six, seven or more introduced in vivo glycosylation sites, preferably introduced by one or more substitutions described in any of the above lists.

Removal and/or introduction of in vitro glycosylation sites may be achieved as described in the subsequent sections on modification of the IFNG polypeptide to introduce and/or remove polymer attachment sites.

Any of the glycosylated BEG polypeptides disclosed in the present section having introduced and/or removed at least one glycosylation site might further be conjugated to a second non-polypeptide moiety. For instance, the second non-polypeptide moiety is a polymer molecule, such as PEG, or any other non-polypeptide moiety. For this purpose the conjugation may be achieved by use of attachment groups already present in the IFNG polypeptide or attachment groups may have been introduced and/or removed, in particular such that a total of 1–6, in particular 34 or 1, 2, 3, 4,–5, or 6 attachment groups are available for conjugation. Preferably, in a conjugate of the invention wherein the IFNG polypeptide comprises two glycosylation sites, the number and molecular weight of the non-polypeptide moiety is chosen so as that the total molecular weight added by the non-polypeptide moiety is in the range of 20–40 kDa, in particular about 20 kDa or 30 kDa.

In particular, the glycosylated IFNG polypeptide may be conjugated to a polymer having cysteine as an attachment group. For this purpose one or more cysteine residues are inserted into the IFNG polypeptide, e.g. as described in the section entitled "Conjugate of the invention, wherein the non-polypeptide moiety is a molecule that has cysteine as an attachment group".

Alternatively or additionally, the glycosylated IFNG polypeptide may be conjugated to a polymer having lysine as an attachment group. For this purpose one or more lysine residues of the parent polypeptide may have been removed, e.g. by any of the substitutions mentioned in the section entitled "Conjugate of the invention, wherein the non-polypeptide moiety is a molecule which has lysine as an attachment group". Alternatively or additionally, a lysine residue may have been introduced, e.g. by any of the substitutions mentioned in said section.

As an alternative to polymer conjugation via a cysteine or lysine group, the conjugation may be achieved via an acid group as described in the section entitled "Conjugation of the invention wherein the non-polypeptide moiety binds to an acid group", or via any other suitable group.

Conjugate of the Invention, wherein the First Non-polypeptide Moiety is a Polymer In an alternative embodiment the first non-polypeptide moiety is a polymer, e.g. any of those described in the section entitled "Conjugation to a polymer molecule", in particular a linear or branched PEG molecule, e.g. having cysteine, lysine, aspartic acid and glutamic acid as an attachment group. Introduction and/or removal of attachment groups for such polymer is illustrated in the following sections. The IFNG polypeptide part of a conjugate according to this embodiment may be a glycosylated polypeptide, e.g. using one or both of the natural N-glycosylation sites of huIFNG or an introduced glycosylation site as described in the immediately preceding section.

Conjugate of the Invention wherein the Non-polypeptide Moiety is a Molecule which has Cysteine as an Attachment Group In a preferred embodiment the first non-polypeptide moiety is a polymer which has cysteine as an attachment group and at least one cysteine residue is introduced into a position of the IFNG polypeptide that in wildtype human IFNG is occupied by a surface exposed amino acid residue. Preferably, the cysteine residue is introduced in accordance with the general consideration for introducing and/or removing attachment groups for the non-polypeptide moiety given in the section entitled "Conjugate of the Invention". For instance, the IFNG polypeptide may comprise at least one substitution selected from the group consisting of P3C, K6C, N10C, K13C, N16C, D21C, N25C, G26C, G31C, K34C, K37C, E38C, E39C, K55C, K59C, N59C, D62C, Q64C, S65C, K68C, E71C, E75C, N83C, S84C, K86C, K87C, K94C, N97C, S99C, T101C, D102C, L103C and N104C (introduction of a cysteine residue in a position that is occupied by an amino acid residue having more than 50% of its side chain exposed to the surface in a structure with receptor). The substitutions N25C and N97C are of particular interest, and especially N25C+N97C, when the IFNG polypeptide is expressed in a non-glycosylating host cell, such as E. coli, since N25 and N97 constitute part of an inherent glycosylation site of huIFNG.

Also or alternatively, the IFNG polypeptide according to this embodiment may comprise at least one cysteine residue introduced in a position occupied by any of the amino acid residues 121–143 of huIFNG.

Preferably, the IFNG polypeptide of the conjugate according to this aspect comprises a total of 1–8, such as 2–6 Cys residues, e.g. 1–3 Cys residues per monomer.

The conjugation between the polypeptide and the polymer may be achieved in any suitable manner, e.g. as described in the section entitled "Conjugation to a polymer molecule", e.g. in using a one step method or in the stepwise manner referred to, in said section. When the conjugate comprises two or more first non-polypeptide moieties, normally each of these has a molecular weight of 5 or 10 kDa. A suitable polymer is VS-PEG.

Conjugate of the Invention, wherein the Non-polypeptide Moiety is a Molecule which has Lysine as an Attachment Group In accordance with this embodiment the non-polypeptide is a polymer having lysine as an attachment group and the IFNG polypeptide is modified in that at least one lysine residue is removed, the lysine residue being selected from the group consisting of K6, K12, K13, K34, K37, K43, K35, K38, K61, K68, K74, K80, K86, K37, K88, K94, K108, K125, K128 and K130, the numbering being made relative to SEQ ID NO 2. More preferably, at least one lysine residue selected from the group consisting of K12, K34, K37, K108, K128 and K130 be removed. Thereby, conjugation of this/these residues can be avoided. The lysine residue(s) may be replaced with any other amino acid residue, but is preferably replaced by an arginine or a glutamine.

Furthermore, the IFNG polypeptide may be modified to have introduced one or more lysine residues, in particular in a position of huIFNG occupied by a surface exposed amino acid residue. Preferably, the lysine residue is introduced in accordance with the general consideration for introducing and/or removing attachment groups for the non-polypeptide moiety given in the section entitled "Conjugate of the Invention", in particular in a position which is occupied by an amino acid residue having at least 25%, such as at least 50% of its side chain exposed to the surface (such positions being identified in the Materials and Methods section herein). Also, at least one lysine residue may be introduced by substitution of any of the amino acid residues 121–143 of SEQ ID NO 2. Alternatively, the IFNG polypeptide may comprise a lysine in at least one position selected from the group consisting of D2,E7, E9, H19, D21, D24, N25, E38, E39, D41, R42, D62, D63, E71, E75, D76, R89, D90, D91, E93, N97, R107, H111, E12, E119, R129, R131, R137, R139 and R140 of SEQ ID NO 2 (positions occupied by an N, R, D; E or H residue in huIFNG).

In accordance with this embodiment, the IFNG polypeptide comprises a substitution in one or more of the above positions, in particular in 1–15, such as 1–8 or 2–8, preferably 1–5 or 2–5 positions (removal and/or introduction of lysine residues) per monomer. For instances, the IFNG polypeptide may comprise a substitution in 1, 2, 3, 4, 5, 6, 7, 8, 9, 10, 11, 12, 13, 14 or 15 of the above positions. The substitutions N25K and N97K are of particular interest, and especially N25K+N97K when the IFNG polypeptide is expressed in a non-glycosylating host cell, such as E. coli, since N25 and N97 constitute part of an inherent glycosylation site of huIFNG.

For instance, the IFNG polypeptide of the conjugate according to this embodiment may comprise at least one of the above substitutions for introduction of a lysine residue in combination with at least one substitution removing a lysine residue as defined above (preferably a substitution to R or Q). For instance, the IFNG polypeptide comprises at least one of the following substitutions N25K and N97K in combination with at least one of the substitutions K128R, K128Q, K130R and K130Q. Even more specifically, the IFNG polypeptide comprises the substitution N25K+ K128R, N25K+K130R, N25K+K128R+K130R, N97+ K128R, N97K+K130R, N97K+K128R+K130R, N25K+ N97K+K129R+K130R, N25K+N97K+K128R and N25K+ N97K+K130R.

While the non-polypeptide moiety of the conjugate according to this aspect of the invention may be any molecule which, when using the given conjugation method has lysine as an attachment group (such as a sugar moiety, a lipophilic group or an organic derivatizing agent), it is preferred that the non-polypeptide moiety is a polymer molecule. The polymer molecule may be any of the molecules mentioned in the section entitled "Conjugation to a polymer molecule", but is preferably selected from the group consisting of linear or branched polyethylene glycol or polyalkylene oxide. Most preferably, the polymer molecule is SS-PEG, NPC-PEG, aldehyd-PEG, MPEG-SPA, mPEG-SCM or mPEG-BTC from Shearwater Polymers Inc., SC-PEG from Enzon Inc., tresylated mPEG as described in U.S. Pat. No. 5,880,255 or oxycarbonyl-oxy-N-dicarboxyimide-PEG (U.S. Pat. No. 5,122,614). Normally, for conjugation to a lysine residue the non-polypeptide moiety has a Mw of about 5 or 10 kDa.

Conjugate of the Invention wherein the Non-polypeptide Moiety Binds to an Acid Group In a still further embodiment the non-polypeptide moiety of the conjugate of the invention is a molecule which has an acid group as the attachment group, and the IFNG polypeptide comprises an amino acid sequence that differs from the amino acid sequence shown in SEQ ID NO 2 in that at least one surface exposed amino acid residue has been substituted with an aspartic acid residue or a glutamic acid residue, preferably in accordance with the general considerations given in the section entitled "Conjugate of the Invention". Alternatively, the Asp or Glu residue may be introduced in a position of the parent IFNG polypeptide occupied by K, R, Q or N. For instance, N25, N97, K125, K178, R129, K130 and/or R131, more preferably N25 and/or N97, most preferably N25+N97, may be substituted with an Asp or Glu residue.

Analogously to what has been described in the previous sections one or more Asp or Glu residues may be removed, e.g. from the receptor binding site, in case the non-polypeptide moiety is one that binds to those residues.

While the non-polypeptide moiety of the conjugate according to this aspect of the invention, which has an acid group as an attachment group, can be any non-polypeptide moiety with such property, it is presently preferred that the non-polypeptide moiety is a polymer molecule or an organic derivatizing agent, in particular a polymer molecule, and the conjugate is prepared, e.g., as described by Sakane and Pardridge, Pharmaceutical Research, Vol. 14, No. 8, 1997, pp 1085–1091.

Non-polypeptide Moiety of the Conjugate of the Invention

As indicated further above the non-polypeptide moiety of the conjugate of the invention is preferably selected from the group consisting of a polymer molecule, a lipophilic compound, a sugar moiety (e.g. by way of in viva glycosylation) and an organic derivatizing agent. All of these agents may confer desirable properties to the polypeptide part of the conjugate, in particular increased functional in vivo half-life and/or a reduced immunogenicity. The polypeptide part of the conjugate is normally conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivating agent and a sugar moiety, to a lipophilic group and a polymer molecule, etc. The conjugation to two or more different non-polypeptide moieties may be done simultaneous or sequentially.

Methods of Preparing a Conjugate of the Invention

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

The polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamine, a carotenoide or steroide, or a synthetic compound such as a carbon acid, an alcohol, an amine and sulphonic acid with one or more alkyl-, aryl-, alkenyl- or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of 300–100,000 Da, such as 300–20,000 Da, more preferably in the range of 500–10,000 Da, even more preferably in the range of 500–5000 Da.

Examples of homo-polymers include a polyol (i.e. poly-OH), a polyamine (i.e. poly-$NH_2$) and a polycarboxylic acid (i.e. poly-COOH). A heteropolymer is a polymer, which comprises one or more different coupling groups, such as, e.g., a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), polycarboxylate, poly-(vinylpyrolidone), polyethylene-co-maleic acid anhydride, polystyrene-co-malic acid anhydride, dextran including carboxymethyl-dextan, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared, e.g., to polysaccharides such as dextran, and the like. In particular, monofunctional PEG, e.g monomethoxy-polyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (Hz), thiol, succinate (SUC), succinimidyl succinate (SS), succinimidyl succinamide (SSA), succinimidyl proprionate (SPA), succinimidy carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Shearwater Polymers, Inc., Huntsville, Ala., USA. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NXS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEGI, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which references are incorporated herein by reference. Furthermore, the following publications, incorporated herein by reference, disclose useful polymer molecules and/or PEGylation chemistries: U.S. Pat. Nos. 5,824,778, 5,476,653, WO 97/32607, EP 229,108, EP 402,378, U.S. Pat. Nos. 4,902,502, 5,281,698, 5,122,614, 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98141562, WO 98/48837, WO 99/32134, WO 99/32139, WO 99/32140, WO 96/40791, WO 98132466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic press, New York). The skilled person will be aware that the activation method and/or conjugation chemistry to be used depends on the attachment group(s) of the IFNG polypeptide as well as the functional groups of the polymer (e.g. being amino, hydroxyl, carboxyl, aldehyde or sulfydryl). The PEGylation may be directed towards conjugation to all available attachment groups on the polypeptide (i.e. such attachment groups that are exposed at the surface of the polypeptide) or may be directed towards specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form (e.g. whether they are linear or branched) of such molecules, and where in the polypeptide such molecules are attached. For instance, the molecular weight of the polymer to be used may be chosen on the basis of the desired effect to be achieved. For instance, if the primary purpose of the conjugation is to achieve a conjugate having a high molecular weight (e.g. to reduce renal clearance) it is usually desirable to conjugate as few high Mw polymer molecules as possible to obtain the desired molecular weight. When a high degree of epitope shielding is desirable this may be obtained by use of a sufficiently high number of low molecular weight polymer (e.g. with a molecular weight of about 5,000 Da) to effectively shield all or most epitopes of the polypeptide. For instance, 2–3, such as 3–6 such polymers may be used.

In connection with conjugation to only a single attachment group on the protein (as described in U.S. Pat. No. 5,985,265), it may be advantageous that the polymer molecule, which may be linear or branched, has a high molecular weight, e.g. about 20 kDa.

Normally, the polymer conjugation is performed under conditions aiming at reacting all available polymer attachment groups with polymer molecules. Typically, the molar ratio of activated polymer molecules to polypeptide is 100-1, in particular 200-1, preferably 100-1, such as 10-1 or 5-1 in order to obtain optimal reaction. However, also equimolar ratios may be used.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578–3581; U.S. Pat. No. 4,179,337; Shafer et al., (1986), J. Polym. Sci. Polym. Chem. Ed., 24, 375–378.

Subsequent to the conjugation residual activated polymer molecules are blocked according to methods known in the art, e.g. by addition of primary amine to the reaction mixture, and the resulting inactivated polymer molecules removed by a suitable method.

Coupling to a Sugar Moiety

The coupling of a sugar moiety may take place in vivo or in vitro. In order to achieve in vivo glycosylation of a polypeptide with IFNG activity, which have been modified so as to introduce one or more in vivo glycosylation sites (see the section "Conjugates of the invention wherein the non-polypeptide moiety is a sugar moiety"), the nucleotide sequence encoding the polypeptide part of the conjugate must be inserted in a glycosylating, eukaryotic expression host. The expression host cell may be selected from fungal (filamentous fungal or yeast), insect or animal cells or from transgenic plant cells. Furthermore, the glycosylation may be achieved in the human body when using a nucleotide sequence encoding the polypeptide part of a conjugate of the invention or a polypeptide, of the invention in gene therapy. In one, embodiment the host cell is a mammalian cell, such as an CHO cell, BHK or HEK cell, e.g. HEK293, or an insect cell, such as an SF9 cell, or a yeast cell, e.g. *Saccharomyces cerevisiae, Pichia pasroris* or any other suitable glycosylating host, e.g. as described further below. Optionally, sugar moieties attached co the IFNG polypeptide by in vivo glycosylation are further modified by use of glycosyltransferases, e.g. using the, glycoAdvance™ technology marketed by Neose, Horsham, Pa., USA. Thereby, it is possible to, e.g., increase the sialyation of the glycosylated IFNG polypeptide following expression and in vivo glycosylation by CHO cells.

Covalent in vitro coupling of glycosides to amino acid residues of IFNG may be used to modify or increase the number or profile of carbohydrate substituents. Depending on the coupling mode used, the sugar(s) may be attached to a) arginine and histidine, b) free carboxyl groups, c) free sulfhydryl groups such as those of cysteine, d) free hydroxyl groups such as those of serine, threonine, cyrosine or hydroxyproline, e) aromatic residues such as those of phenylalanine or tryptophan or f) the amide group of glutamine. These amino acid residues constitute examples of attachment groups for a sugar moiety, which may be introduced and/or removed in the IFNG polypeptide of the conjugate of the invention. Suitable methods of in vitro coupling are described, for example in WO 87/05330 and in Aplin et al., CRC Crit Rev. Biochem., pp. 259–306, 1981. The in vitro coupling of sugar moieties or PEG to protein- and peptide-bound Gln-residues can also be carried out by transglutaminases (TGases), e.g. as described by Sato et al., 1996 Biochemisty 35, 13072–13080 or in EP 725145.

Coupling to an Organic Derivatizing Agent

Covalent modification of the IFNG polypeptide may be performed by reacting (an) attachment group(s) of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamdomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonateat pH 5.5–7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with thee agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl) are selectively modified by reaction with carbodiimides (R—N═C═N—R'), where R and R' are different alkyl groups, such as 1-cyclohexyl-3-(7-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of Functional Site

It has been reported that excessive polymer conjugation can lead to a loss of activity of the polypeptide to which the polymer is conjugated. This problem can be eliminated, e.g., by removal of attachment groups located at the functional site or by blocking the functional site prior to conjugation. These latter strategies constitute further embodiments of the invention (the first strategy being exemplified further above, e.g. by removal of lysine residues which may be located close to the functional site). More specifically, according to the second strategy the conjugation between the polypeptide and the on-polypeptide moiety is conducted under conditions where the functional site of the IFNG polypeptide is blocked by a helper molecule capable of binding to the functional site of the polypeptide. Preferably, the helper molecule is one, which specifically recognizes a functional site of the polypeptide, such as a receptor. Alternatively, the helper molecule may be an antibody, in particular a monoclonal antibody recognizing the polypeptide exhibiting IFNG activity. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such, as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, a sugar moiety, an organic derivatizing agent or any other compound is conducted in the normal way, e.g. as described in the sections above entitled "Conjugation to . . . ".

In a further embodiment the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art, e.g. as described in the sections above entitled "Conjugation to . . .". This procedure allows the polypeptide conjugate to be separated from the helper molecule by elution. The polypeptide conjugate is eluated by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule may be derivatized with a second molecule (e.g. biotin) that can be recognized by a specific binder (e.g. streptavidin). The specific binder may be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. De-protection may be achieved by providing conditions in which the helper molecule dissociates from the functional site of the IFNG to which it is bound. For instance, a complex between an antibody to which a polymer is conjugated and an anti-idiotypic antibody can be dissociated by adjusting the pH to an acid or alkaline pH.

Conjugation of a Tagged Polypeptide In an alternative embodiment the IFNG polypeptide is expressed, as a fusion protein, with a tag, i.e. an amino acid sequence or peptide stretch made up of typically 1–30, such as 1–20 amino acid residues. Besides allowing for fast and easy purification, the tag is a convenient tool for achieving conjugation between the tagged IFNG polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged IFNG polypeptide in, e.g., microtiter plates has the advantage that the tagged polypeptide can be immobilised in the microtiter plates directly from the culture broth, (in principle without any purification) and subjected to conjugation. Thereby, the total number of process steps (from expression to conjugation) can be reduced. Furthermore, the tag may function as a spacer molecule ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g. from Unizyme Laboratories, Denmark. For instance, the tag may any of the following sequences:

His-His-His-His-His-His
Met-Lys-His-His-His-His-His-His
Met-Lys-His-Ala-His-His-Gln-His-His
Met-Lys-His-Gln-His-Gln-His-Gin-His-Gln-His-Gln-His-Gln (all available from Unizyme Laboratories, Denmark)

or any of the following:

EQKLI SEEDL (a C-terminal tag described in Mol. Cell. Biol. 5:3610–16, 1985)
DYKDDDDK (a C- or N-terminal tag)
YPYDVPDYA Antibodies against the above tags are commercially available, e.g. from ADI Aves Lab and Research Diagnostics.

A convenient method for using a tagged polypeptide for PEGylation is given, in the Materials and Methods section below.

The subsequent cleavage of the tag from the polypeptide may be achieved by use of commercially available enzymes.

Polypeptides of the Invention

In a further aspect the invention relates to generally novel IFNG polypeptides as disclosed herein. The novel polypeptides are important intermediate compounds for the preparation of a conjugate of the invention. In addition, the polypeptides themselves may have interesting properties.

For instance, the novel IFNG polypeptide comprises at least one substitution to K, R D, E, C, S, T or N of a surface exposed amino acid residue as described in much further detail in the preceding part of the application.

Methods of Preparing an IFNG Polypeptide

The IFNG polypeptide, optionally in glycosylated form, may be produced by any suitable method known in the art. Such methods include constructing a nucleotide sequence encoding the polypeptide and expressing the sequence in a suitable transformed or transfected host. However, polypeptides of the invention may be produced, albeit less efficiently, by chemical synthesis or a combination of chemical synthesis or a combination of chemical synthesis and recombinant DNA technology.

The nucleotide sequence of the invention encoding an IFNG polypeptide (in monomer or single chain form) may be constructed by isolating or synthesizing a nucleotide sequence encoding the parent IFNG, such as huIFNG with the amino acid sequence SEQ ID NO 2, and then changing the nucleotide sequence so as to effect introduction (i.e. insertion or substitution) or deletion (i.e. removal or substitution) of the relevant amino acid residue(s).

The nucleotide sequence is conveniently modified by site-directed mutagenesis in accordance with well-known methods, see, e.g., Mark et al., "Site-specific Mutagenesis of the Human Fibroblast Interferon Gene", Proc. Natl. Acad. Sci. USA, 81, pp. 5662–66 (1984); and U.S. Pat. No. 4,588,585.

Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produces. For example, several small oligonucleotides coding for portions of the desired polypeptide may be synthesized and assembled by PCR, ligation or ligation chain reaction (LCR). The individual oligonucleotides typically contain 5' or 3' overhangs for complementary assembly.

Once assembled (by synthesis, site-directed mutagenesis or another method), the nucleotide sequence encoding the polypeptide is inserted into a recombinant vector and operably linked to control sequences necessary for expression of the IFNG in the desired transformed host cell.

It should of course be understood that not all vectors and expression control sequences function equally well to express the nucleotide sequence encoding an IFNG polypeptide described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the IFNG polypeptide is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pCDNA3.1 (+)\Hyg (Invitrogen, Carlsbad, Calif., USA) and pCI-neo (Stratagene, La Jola. Calif., USA). Useful expression vectors for bacterial hosts include known bacterial plasmids, such as plasmids from E. coli, including pBR322, pET3a and pET12a (both from Novagen Inc., Wisconsin, USA), wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof, the POT1 vector (U.S. Pat. No. 4,931,373), the pJSO37 vector described in (Okkels, Ann. New York Acad. Sci. 782, 202–207, 1996) and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685–98 (1986), pBluebac 4.5 and pMelbac (both available from Invitrogen).

Other vectors for use in this invention include those that allow, the nucleotide sequence encoding the IFNG polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304–19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1–3 and origin of replication.

The vector may also comprise a selectable marker, e.g. a gene the product of which complements a defect in the host cell, such as the gene coding for dihydrofolate reductase (DER) or the Schizosaccharomyces pombe TPI gene (described by P. R. Russell, Gene 40, 1985, pp. 125–130), or one which confers resistance to a drug, e.g. ampicillin, kanamycin, tetracyclin, chloramphenicol, neomycin, hydromycin or methotrexate. For filamentous fungi, selectable markers include amdS, pyrG, arcB, niaD sC.

The term "control sequences" is defined herein to include all components, which are necessary or advantageous for the expression of the IFNG polypeptide. Each control sequence may be native or foreign to the nucleic acid sequence encoding the polypeptide. Such control sequences include, but are not limited to, a leader, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the Drosophila minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. J. Mol Biol 1987 August 20;196(4):947–50).

In order to improve expression in mammalian cells a synthetic intron may be inserted in the 5' untranslated region of the nucleotide sequence encoding the IFNG polypeptide. An example of a synthetic intron is the synthetic intron from the plasmid pCI-Neo (available from Promega Corporation, Wisconsin, USA).

Examples of suitable control sequences for directing transcription in insect cells include the polyhedrin promoter, the P10 promoter, the Autographa californica polyhedrosis virus basic protein promoter, the baculovirus immediate early gene 1 promoter and the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydogenase genes, the ADH2-4c promoter and the inducible GAL promoter.

Examples of suitable control sequences for use in filamentous fungal host cells include the ADH3 promoter and terminator, a promoter derived from the genes encoding Aspergillus oryzae TAKA amylase triose phosphate isomerase or alkaline protease, an A. niger α-amylase, A. niger or A. nidulans glucoamylase, A. nidulans acetamidase, Rhizomucor miehei aspartic proteinase or lipase, the TPI1 terminator and the ADH3 terminator.

Examples of suitable control sequences for use in bacterial host cells include promoters of the lac system, the trp system, the TAC or TRC system and the major promoter regions of phage lambda.

The nucleotide sequence of the invention, whether prepared by site-directed mutagenesis, synthesis or other methods, may or may not also include a nucleotide sequence that encode a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with huIFNG) or heterologous (i.e. originating from another source than huIFNG) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as E. coli, or eukaryotic, e.g. derived from a mammalian, or insect or yeast cell.

The presence or absence of a signal peptide will, e.g., depend on the expression host cell used for the production of the, polypeptide, the protein to be expressed (whether it is an intracellular or intracellular protein) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the lepidopteran *Manduca sexta* adipokinetic hormone precursor, (cf. U.S. Pat. No. 5,023,328), the honeybee melittin (Initrogen), ecdysteroid UDPglucosyltransferase (egt) (Murphy et al., Protein Expression and Purification 4, 349–337 (1993) or human pancreatic lipase (hpl) (Methods in Enzymology 284, pp. 262–272, 1997).

A preferred signal peptide for use in mammalian cells is that of huIFNG or the, murine Ig kappa light chain signal peptide (Coloma, M (1992) J. Imm. Methods 152:89–104). For use in yeast cells suitable signal peptides have been found to be the α-factor signal peptide from *S. cereviciae*. (cf. U.S. Pat. No. 4,870,008), the signal peptide of mouse salivary amylase (cf. O. Hagenbuchle et al., Nature 289, 1981, pp. 643–646), a modified carboxypeptidase; signal peptide (cf. L. A. Valls at al., Cell 48, 1987, pp. 887–897), the yeast BAR1 signal peptide (cf. WO 87/02670), and the yeast aspartic protease 3 (YAP3) signal peptide (cf. M. Egel-Mitani et al., Yeast 6, 1990, pp. 127–137).

Any suitable host may be used to product the IFNG polypeptide, including bacteria, fungi (including yeasts), plant, insect, mammal, or other appropriate animal cells or cell lines, as well as transgenic animals or plants. Examples of bacterial host cells include grampositive bacteria such as strains of *Bacillus*, e.g. *B. brevis* or *B. subtilis*, *Pseudomonas* or *Streptomyces*, or gramnegative bacteria, such as strains of *E. coli*. The introduction of a vector into a bacterial host cell may, for instance, be effected by protoplast transformation (see, e.g., Chang and, Cohen, 1979, *Molecular General Genetics* 168: 111–115), using competent cells (see, e.g., Young and Spizizen, 196 1, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Generics and Molecular Biology, Method in Enzymology*, Volume 194, pp, 182–187, Academic Press, Inc., New York; Ito et al., 1983, *Journal of Bacteriology* 153: 163; and Hinnen at al., 1979, *Proceedings of the National Academy of Sciences USA* 75: 1920.

Examples of suitable yeast host cells include strains of *Saccharomyces*, e.g. *S. cerevisiae*, *Schizosaccharomyces*, *Kluyveromvaces*, *Pichia*, such as *P. pastoris* or *P. methanolica*, *Hansenula*, such as *H. Polymorpha* or *Yarrowia*. Methods for transforming yeast cells with heterologous DNA and producing heterologous polypeptides therefrom are disclosed by Clontech Laboratories, Inc, Palo Alto, Calif., USA (in the product protocol for the Yeastmaker™ Yeast Transformation System Kit), and by Reeves et al., FEMS Microbiology Letters 99 (1992) 193–198, Manivasakam and Schiestl, Nucleic Acids Research, 1993, Vol. 21, No. 18, pp. 4414–4415 and Ganeva et al., FEMS Microbiology Letters 121 (1994) 159–164.

Examples of suitable insect host cells include a *Lepidoptora* cell line, such as *Spodoptera frugiperda* (Sf9 or Sf21) or *Trichoplusioa ni* cells (High Five) (U.S. Pat. No. 5,077, 214). Transformation of insect cells and production of heterologous polypeptides therein may be performed as described by Invitrogen.

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the IFNG polypeptide.

Methods for introducing exogenous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc, Totowa, N.J., USA and Hannson M A and Rae I F, General Techniques of Cell Culture, Cambridge University Press 1997).

In order to produce a glycosylated polypeptide a eukaryotic host call, e.g. of the type mentioned above, is preferably used.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered, by methods known in the art. For example, the polypeptide may be recovered from the nutrient medium by conventional procedures including, but not limited to, centrifugation, filtration, extraction, spray dying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989). Specific methods for purifying polypeptides exhibiting IFNG activity are disclosed in EP 110044 and unexamined Japanese patent application No. 186995/84.

The biological activity of the IFNG polypeptide can be assayed by any suitable method known in the art. Such assays include antibody neutralization of antiviral activity, induction of protein kinase, oligoadenylate 2,5-A synthetase or phosphodiesterase activities, as described in EP 41313 B1. Such assays also include immunomodulatory assays (see, e.g., U.S. Pat. No. 4,753,795), growth inhibition assays, and measurement of binding to cells that express interferon receptors. Specific assays are described in the Materials and Methods section herein.

Furthermore, the invention relates to improved methods of treating, in particular, interstitial lung diseases, but also granulomatous diseases, cancer, infections, bone disorders (e.g. a bone metabolism disorder so as malignant osteopetrosis) and autoimmune diseases such as rheumatoid arthritis, the key advantages being less frequent and/or less intrusive administration of more efficient therapy, and optionally a lower risk of immune reactions with the therapeutically active compound(s).

The conjugate of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art (Remington's Pharmaceutical Sciences, 18th edition, A. R. Gennaro, Ed., Mack Publishing Company [1990]; Pharmaceutical Formulation Development of Peptides and Proteins, S. Frokjaer and L Hovgaard, Eds., Taylor & Francis [2000] and Handbook of Pharmaceutical Excipients, 3rd edition, A. Kibbe, Ed., Pharmaceutical Press [2000]).

The conjugate of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

The conjugate of the invention is administered at a dose approximately paralleling that employed in therapy with known commercial preparations of IFNG such as Actimmune or as specified in EP 795332. The exact dose to be administered depends on the circumstances. Normally, the dose should be capable of preventing or lessening the severity or spread of the condition or indication being treated. It will be apparent to those of skill in the art that an effective amount of conjugate or composition of the invention depends, inter alia, upon the disease, the dose, the administration schedule, whether the polypeptide or conjugate or composition is administered alone or in conjunction with other therapeutic agents, the serum half-life of the compositions, and the general health of the patient.

The invention also relates to the use of a) a conjugate comprising at least one non-polypeptide moiety covalently attached to an IFNG polypeptide, the IFNG polypeptide being selected from the group consisting of huIFNG, rhuIFNG or an IFNG polypeptide as described herein (i.e. the conjugate being a conjugate of the invention) or b) a pharmaceutical composition of the invention, for the manufacture of a medicament, a pharmaceutical composition or a kit-of-parts for the treatment of interstitial lung diseases, cancer, infections, bone disorders (e.g. a bone metabolism disorder so as malignant osteopetrosis) and/or inflammatory diseases, in particular interstitial lung diseases, most particularly idiopathic pulmonary fibrosis. A glucocorticoid such as prednisolone may also be included. The preferred dosing is 1–4, more preferably 2–3, micrograms/kg patient weight of the polypeptide component per dose. The preferred dosing is 100–350, more preferably 100–150 micrograms glucocorticoid/kg patient weight per dose.

Also disclosed are improved means of delivering the molecules or preparations, optionally additionally comprising glucocorticoids.

The invention also relates to a kit of parts suitable for the treatment of interstitial lung diseases comprising a first pharmaceutical composition comprising the active components a) or b) mentioned above and a second pharmaceutical composition comprising at least one glucocorticoid, each optionally together with a pharmaceutically acceptable carrier and/or excipient.

The conjugate of the invention can be formulated into pharmaceutical compositions by well-known methods. Suitable formulations are described by Remington's Pharmaceutical Sciences by E. W. Martin and U.S. Pat. No. 5,183,746.

The pharmaceutical composition may be formulated in a variety of forms, including liquid, gel, lyophilized, powder, compressed solid, or any other suitable form. The preferred form will depend upon the particular indication being treated and will be apparent to one of skill in the art.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The formulations can be administered continuously by infusion, although bolus injection is acceptable, using techniques well known in the art, such as pumps or implantation. In some instances the formulations may be directly applied as a solution or spray. The preferred mode of administration will depend upon the particular indication being treated and will be apparent to one of skill in the art.

The pharmaceutical composition of the invention may be administered in conjunction with other therapeutic agents. These agents may be incorporated as part of the same pharmaceutical composition or may be administered separately from the polypeptide or conjugate of the invention, either concurrently or in accordance with any other acceptable treatment schedule. In addition, the polypeptide, conjugate or pharmaceutical composition of the invention may be used as an adjunct to other therapies. In particular, combinations with glucocorticoids as described in EP 795332 are considered.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM Suitable-buffering agents for use with the present invention include both organic and inorganic acids and salts thereof such as citrate buffers (e.g., monosodium citrate-disodium citrate mixture, citric acid-trisodiunm citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tatrate buffers (e.g., tartaric acid-sodium tartrate mixture, tartaric acid-potassium tartrate mixture, tartaric acid-sodium hydroxide mixture. etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, hisidine buffers and trimethylamine salts such as Tris.

Preservatives are added to retard microbial growth, and are typically added in amounts of about 0.2%–1% (w/v). Suitable preservatives for use with the present invention include phenol, benzyl alcohol, meta-cresol, methyl paraben, propyl paraben, octadecyidimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, omithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents. The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nano-particles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

Sustained Release Preparations

Suitable examples of sustained-release preparations include semi-permeable matrices of solid hydrophobic polymers containing the conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot®9 (injectable microspheres composed of lactic acid-glycolic acid copolymer and leuprolide acetate), and poly-D-(-)-3-hydroxybutyric acid. While polymers such as ethylenevinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intennolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The conjugates may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Topical Administration

Formulations suitable for topical administration include liquid or semi-liquid preparations suitable for penetration through the skin (e.g., liniments, lotions, ointments, creams, or pastes) and drops suitable for administration to the eye, ear, or nose.

Pulmondry Delivery

Formulations suitable for use with a nebulizer, either jet or ultrasonic, will typically comprise the polypeptide or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570 and U.S. Pat. No. 5,522,385 which are hereby incorporated by reference.

Formulations for use with a metered dose inhaler device will generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugar or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid nay also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers will comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/$cm^2$ having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass.

The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkermes, Cambridge, Mass.; and the AERx pulmonary drug delivery system manufactured by Aradigm Corporation, Hayward, Calif.

The invention provides compositions and methods for treating bacterial and viral infections, cancers or tumors, interstitial pulmonary diseases such as idiopathic pulmonary fibrosis, granulomatous diseases, bone disorders (e.g. a bone metabolism disorder so as malignant osteopetrosis) and autoimmune diseases such rheumatoid arthritis.

In a further aspect the invention relates to a method of treating a mammal having circulating antibodies against huIFNG or rhuIFNG, which method comprises administering a compound which has the bioactivity of IFNG and which does not react with said antibodies. The compound is preferably a conjugate as described herein and the mammal is preferably a human being. The mammals to be treated may suffer from any of the diseases listed above for which IFNG is a useful treatment. Furthermore, the invention relates to a method of making a pharmaceutical product for use in treatment of mammals having circulating antibodies against huIFNG or rhuIFNG, wherein a compound which has the bioactivity of IFNG and which does not react with such is formulated into an injectable or otherwise suitable formulation. The term "circulating antibodies" is intended to indicate autoantibodies formed in a mammal in response to having been treated with any of the commercially available IFNG preparations.

Also contemplated is use of a nucleotide sequence encoding an IFNG polypeptide of the invention in gene therapy applications. In particular, it may be of interest to use a nucleotide sequence encoding an IFNG polypeptide described in the section above entitled "Glycosylated Polypeptides of the Invention modified to incorporate additional glycosylation sites". The lycosylation of the polypeptide is thus achieved during the course of the gene therapy, i.e. after expression of the nucleotide sequence in the human body.

Gene therapy applications contemplated include treatment of those diseases in which the polypeptide is expected to provide an effective therapy.

Local delivery of IFNG using gene therapy may provide the therapeutic agent to the target area while avoiding potential toxicity problems associated with non-specific administration.

Both in vitro and in vivo gene therapy methodologies are contemplated.

Several methods for transferring potentially therapeutic genes to defined cell populations are known. For further reference see, e g., Mulligan, "The Basic Science Of Gene Therapy", Science, 260, pp. 926–31 (1993). These methods include:

Direct gene transfer, e.g. as disclosed by Wolff et al., "Direct Gene transfer Into Mouse Muscle In vivo", Science 247, pp. 1465–68 (1990);

Liposome-mediated DNA transfer, e.g., as disclosed by Caplen et al., "Liposome-mediated CFTR Gene Transfer to the Nasal Epithelium Of Patients With Cystic Fibrosis" Nature Med., 3, pp. 39–46 (1995); Crystal, "The Gene As A Drug", Nature Med., 1, pp.—15–17 (1995); Gao and Huang, "A Novel Cationic Liposome Reagent For Efficient Transfection of Mammalian Cells", Biochem Biophys Res. Comm., 179, pp. 280–85 (1991);

Retrovirus-mediated DNA transfer, e.g., as disclosed by Kay et al., "In vivo Gene Therapy of Hemophilia B: Sustained Partial Correction In Factor IX-Deficient Dogs", Science, 262, pp. 117–19 (1993); Anderson, "Human Gene Therapy", Science, 256, pp. 808–13(1992);

DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses as Vectors for Gene Therapy", Gene Therapy, 1, pp. 367–84 (1994); U.S. Pat. No. 4,797,368, and U.S. Pat. No. 5,139,941.

The invention is further described in the following examples. The examples should not, in any manner, be understood as limiting the generality of the present specification and claims.

MATERIALS AND METHODS

Assays

Interferon Assay Outline

It has previously been published that IFNG interacts with and activates IFNG receptors on HeLa cells. Consequently, transcription is activated at promoters containing an Interferon Stimulated Response Element (ISRE). It is thus possible to screen for agonists of interferon receptors by use of an ISRE coupled luciferase reporter gene (ISRE-luc) placed in HeLa cells.

Primary Assay HeLa cells are co-transfected with ISRE-Luc and pCDNA 3.1/hygro and foci (cell clones) are created by selection in DMEM media containing Hygromycin B. Cell clones are screened for luciferase activity in the presence or absence of IFNG. Those clones showing the highest ratio of stimulated to unstimulated luciferase activity are used in further assays.

To screen muteins, 15,000 cells/well are seeded in 96 well culture plates and incubated overnight in DMEM media. The next day muteins as well as a known standard are added to the cells in various concentrations. The plates are incubated for 6 hours at 37° C. in a 5% $CO_2$ air atmosphere LucLite substrate (Packard Bioscience, Groningen The Netherlands) is subsequently added to each well. Plates are sealed and luminescence measured on a TopCount luminometer (Packard) in SPC (single photon counting) mode. Each individual plate contains wells incubated with IFNG as a stimulated control and other wells containing normal media as an unstimulated control. The ratio between stimulated and unstimulated luciferase activity serves as an internal standard for both mutein activity and experiment-to-experiment variation.

Functional in vivo Half-life of IFNG Conjugate

Measurement of biological half-life can be carried out in number of ways described in the literature. One method described by Rutenfranz et al. (J. Interferon Res. 1990, vol. 10, p. 337–341) who used intravenous and intramuscular injection of IFNG in 8 weeks old C57BL/6 mice. The biological half-life was measured by a biological assay determining the IFNG titer in murine serum, using Hep-2 cells and vesicular stomatitis virus (VVS). As an alternative, they also used ELISA to detect the IFNG level in serum.

As an alternative, radioactive labelled IFNG can be used to study the subcutaneous absorption and local distribution of IFNG. Croos and Roberts (I. Pharm., 1993, vol 45, p. 606–609) have done studies of $^{125}$IFNG in anaesthetized female Sprague-Dawley rats. After administration subcutaneous administration, blood and tissue samples were collected and the amount of IFNG was determined by gamma-counting.

PEGylation of IFNG

PEGylated rhuIFNG may be prepared as described in Example 2 of U.S. Pat. No. 5,109,120. Analogously, modified IFNG polypeptides described herein, e.g. carrying the mutation N25K may be PEGylated. The resulting PEG-IFNG-N25K conjugate has an additional PEG-molecule attached as compared with the conjugate of rhuIFNG.

Preparation of Pharmaceutical Composition

A pharmaceutical composition, e.g. for treatment of interstitial pulmonary diseases may be prepared by formulating the relevant purified conjugate of the invention in injectable compositions according to procedures well known to the man skilled in the art in such a way that each vial comprises conjugate in an amount comprising 50, 100, 200, 300, 400 or 500 micrograms of, e.g., rhuIFNG or IFNG-N25K.

Identification of Surface Exposed Amino Acid Residues

Structures

Experimental 3D structures of huIFNG determined by X-ray crystallography have been reported by: Ealick et al. Science 252:698–702 (1991) reporting an the C-alpha trace of an IFNG homodimer. Walter et. al. Nature 376:230–235 (1995) reporting on the structure of an IFNG homodimer in complex with two molecules of a soluble form of the IFNG receptor. The coordinates of this structure have never been made publicly available. Thiel et.al. Structure 8:927–936 (2000) reporting on the structure of an IFNG homodimer in complex with two molecules of a soluble form of the IFNG receptor having a third molecule of the receptor in the structure not making interactions with the IFNG homodimer.

Methods

Accessible Surface Area (ASA)

The computer program Access (B. Lee and F. M. Richards, J. Mol.Biol. 55: 379–400 (1971)) version 2 (Copyright (c) 1983 Yale University) was used to compute the accessible surface area (ASA) of the individual atoms in the structure. This method typically uses a probe-size of 1.4 Å and defines the Accessible Surface Area (ASA) as the area formed by the centre of the probe. Prior to this calculation all water molecules, hydrogen atoms and other atoms not directly related to the protein are removed from the coordinate set.

Fractional ASA of Side Chain

The fractional ASA of the side chain atoms is computed by division of the sum of the ASA of the atoms in the side chain with a value representing the ASA of the side chain atoms of that residue type in an extended ALA-x-ALA tripeptide. See Hubbard, Campbell & Thornton (1991) J.Mol.Biol.: 220,507–530. For this example the CA atom is regarded as a part of the side chain of Glycine residues but not for the remaining residues. The following table are used as standard 100% ASA for the side chain:

| Ala | 69.23 Å$^2$ |
| --- | --- |
| Arg | 200.35 Å$^2$ |
| Asn | 106.25 Å$^2$ |
| Asp | 102.06 Å$^2$ |
| Cys | 96.69 Å$^2$ |
| Gln | 140.58 Å$^2$ |
| Glu | 134.61 Å$^2$ |
| Gly | 32.28 Å$^2$ |
| His | 147.00 Å$^2$ |
| Ile | 137.91 Å$^2$ |
| Leu | 140.76 Å$^2$ |
| Lys | 162.50 Å$^2$ |
| Met | 156.08 Å$^2$ |
| Phe | 163.90 Å$^2$ |
| Pro | 119.65 Å$^2$ |
| Ser | 78.16 Å$^2$ |
| Thr | 101.67 Å$^2$ |
| Trp | 210.89 Å$^2$ |
| Tyr | 176.61 Å$^2$ |
| Val | 114.14 Å$^2$ |

Residues not detected in the structure are defined as having 100% exposure as they are thought to reside in flexible regions.

Determining Distances Between Atoms:

The distance between atoms was determined using molecular graphics software e.g. InsightII v. 98.0, MSI INC.

Determination of Receptor Binding Site:

The receptor-binding site is defined as comprising of all residues having their accessible surface area changed upon receptor binding. This is determined by at least two ASA calculations; one on the isolated ligand(s) in the ligand(s)/receptor(s) complex and one on the complete ligand(s)/receptor(s) complex.

Result

The X-ray structure used was of an IFNG homo-dimer in complex with two molecules of a soluble form of the IFNG receptor having a third molecule of the IFNG receptor in the structure not making interactions with the IFNG homodimer reported by Thiel et.al. Structure 8:927–936 (2000), The structure consists of the IFNG homodimer wherein the two molecules are labeled A and B. For construction purposes there is an additional methionine placed before the IFNG sequence labeled M0 and the sequence is C-terminally truancuted with ten residues (Q133 being the last residue in the constructed molecules). The M0 is removed from the structure in all the calculations of this example. The structure of the two IFNG monomers has very weak electron density after residue 120 and residues were only modeled until residue T126. Therefore, residues S121–T126 were removed from the structure prior to the calculations in this example. The two receptor fragments labeled C and D make direct interactions with the IFNG homodimer and a third receptor molecule labeled E makes no contact with the IFNG homodimer and are not included in these calculations.

Surface Exposure:

Performing fractional ASA calculations on the homodimer of molecules A and B excluding M0 and S121–T126 in both molecules resulted in the following residues having more than 25% of their side chain exposed to the surface in at least one of the monomers: Q1, D2, P3, K6, E9, N10, K12, K13, Y14, N16, G18, H19, S20, D21, A23, D24, N25, G26, T27, G31, K34, N35, K37, E38, E39, S40, K55, K58, N59, K61, D62, D63, Q64, S65, Q67, K68, E71, T72, K74, E75, N78, V79, K80, N83, S84, N85, K36, K87, D90, E93, K94, N97, S99, T101, D102, L103,N104, H111, Q115, A118 and E119.

The following residues had more than 50% of their side chain exposed to the surface in at least one of the monomers: Q1, D2, P3, K6, E9, N10, K13, N16, G18, H19, S20, D21, A23, D24, N25, G26, T27, G31, K34, K37, E38, E39,K55, K58, N59, D62, Q64, S65, K68, E71, E75, N83, S84, K86, K87, K94, N97, S99, T101, D102, L103, N104, Q115, A118, E119.

Performing fractional ASA calculations on the homodimer of molecules A and B excluding M0 and S121-T126 in both molecules and including the receptor molecules C and D resulted in the following residues had more than 25% of their side chain exposed to the surface in at least one of the monomers: Q1, D2, P3, K6, E9, N10, K13, Y14, N16, G18, H19, D21, N25, G26, G31, K34, N35, K37, E38, E39, S40, K55, K58, N59, K61, D62, D63, Q64, S65, Q67, K68, E71, T72, K74, E75, N78, V79, K80, N83, S84, N85, K86, K87, D90, E93, K94, N97, S99, T101, D102, L103, N104; E119. The following residues had more than 50% of their side chain exposed to the surface in at least one of the monomers: P3, K6, N10, K13, N16, D21, N25, G26, G31, K34, K37, E38, E39, K55, K58, N59, D62, Q64,S65, K68, E71, E75, N83, S84, K86, K87, K94, N97, S99, T101, D102, L103 and N104.

All of the above positions are targets for modification in accordance with the present invention.

Comparing the two lists results in K12, S20, A23, D24, T27, H111, Q115 and A118 being removed from the more than 25% side chain ASA list upon receptor binding, and Q1, D2, E9, G18, E19, S20, A23, D24, T27, Q115, A118 and E119 being removed from the more than 50% side chain ASA list upon receptor binding.

Residues not determined in the structure are treated as fully surface exposed, i.e. residues S121, P122, A123, A124, K125, T126, G127, K128, R129, K130, R131, S132, Q133, M134, L135, F136, R137, G138, R139, R140, A141, S142, Q143. These residues also constitute separate targets for introduction of attachment groups in accordance with the present invention (or may be viewed as belonging to the group of surface exposed amino acid residues, e.g. having more than 25% or more than 50% exposed side chains).

Receptor Binding Site:

Performing ASA calculations as described above results in the following residues of the IFNG molecule having reduced ASA in at least one of the monomers in the complex as compared to the calculation on the isolated dimer. Q1, D2, Y4, V5, E9, K12, G18, H19, S20, D21, V22, A23, D24, N25, G26, T27, L30, K34, K37, K108, H111, E112, I114, Q115, A118, E119.

EXAMPLES

Example 1

Design of an Expression Cassette for Expression of IFNG in Yeast and CHO Cells

The DNA sequence, GenBank accession number X13274, encompassing a full length cDNA encoding mature huIFNG without its native signal peptide, was modified in order to facilitate high expression in yeast cells. First, a MATa signal peptide was introduced instead of the IFNG signalpeptide in order to facilitate secretion into yeast media. Secondly, the codons of the huIFNG nucleotide sequence were modified by making a bias in the codon usage towards the codons frequently used in yeast. Subsequently, certain nucleotides in the sequence were substituted with others in order to introduce recognition sites for DNA restriction endonucleases. Primers were designed such that the gene could be synthesised The primers were assembled to the synthetic gene by one step PCR using Platinum Pfx-polymerase kit (Life Technologies) and standard three step PCR cycling parameters. The assembled gene was amplified by PCR using the same conditions and has the sequence shown in SEQ ID NO 3.

The synthesised gene was cloned into pJSO37-lip Okkels, J. S.(1996) Rec. DNA Biotech. III., vol782, 202–207) between the HindIII site at the 5' end and the XbaI at the 3', resulting in pIGY-1.

In order to make a single-chain construct containing covalently linked monomeric IFNG polypeptides, the following three constructs were made:

I) A construct containing two mature full-length huIFNG polypeptides, linked through a 19mer linker peptide modelled after the human IgA1 hinge regions (Lunn C A et al., J. Biol. Chem., 267, 17920–17924, 1992). This was done by PCR, using the following primers

```
ADJ002 5'-GGTTTGATATCGATGGCCAA-3'                                    (SEQ ID NO 4)

ADJ003 5'-GCGGCCCTCTAGATTACT-3'                                      (SEQ ID NO 5)

ADJ004 5'-CATCTCCGTCCACTCCGACTCCATAGCATGCAAGATCCATATGTGA             (SEQ ID NO 6)
       AAGAA-3'

ADJ007 5'-ATCTTGCATGCTATGGAGTCGGAGTGGACGGAGATGGAGTTGGC                (SEQ ID NO 7)
       GGAGTAGAAGGAACCGCTGTTTTAGCAGCTGGAGACAATT-3'
```

The PCR fragments were cloned in pIGY-1 between ClaI at the 5' end and XbaI at the 3' end assembling the two monomers in SphI (introduced in the linker region). This construct was called pIGY-2.

II) A construct containing two monomeric mature full-length huIFNG polypeptides without linker. For this, the following primers were used for PCR.

```
ADJ002 5'-GGTTTGATATCGATGGCCAA-3'                                    (SEQ ID NO 8)

ADJ003 5'-GCGGCCCTCTAGATTACT-3'                                      (SEQ ID NO 9)

ADJ006 5'-TTTAGAGGTAGAAGAGCTTCTCAGCAAGATCCATATGTGAAAGAAGCT-3'        (SEQ ID NO 10)

ADJ009 5'-AGCTTCTTTCACATATGGATCTTGCTGAGAAGCTCTTCTACGTCTAAA-3'        (SEQ ID NO 11)
```

The PCR fragment was assembled by two-step PCR and cloned between ClaI, at the 5' end, and XbaI at the 3' end in pIGY-1 and named pIGY-3

III) A construct containing two C-terminally truncated (the last 11 amino acids) monomeric IFNG polypeptides covalently linked through the 19-mer peptide linker mentioned above. The following primers were used:

```
ADJ001 5'-TGCTCTAGACATCTGAGATCGTTTTCTCTTTCC-3'                       (SEQ ID NO 12)

ADJ002 5'-GGTTTGATATCGATGGCCAA-3'                                    (SEQ ID NO 13)

ADJ004 5'-CATCTCCGTCCACTCCGACTCCATAGCATGCAAGATCCATA                  (SEQ ID NO 14)
       TGTGAAAGAA-3'

ADJ005 5'ATCTTGCATGCTATGGAGTCGGAGTGGACGGAGATGGAGTT                   (SEQ ID NO 15)
       GGCGGAGTAGAAGGAACCGGCATCTGAGATCTTTTTCTCC-3'
```

The PCR fragments were cloned in pIGY-1 between ClaI at the 5' end and XbaI at the 3' end assembling the two monomers in SphI (introduced in the linker region). This construct was called pIGY4

Constructs for Expression in CHO Cells

To express IFNG in CHO cells, the following oligonucleotide is synthesized to enable cloning of IFNG including it's signal peptide, into pcDNA3.1/hygro (Invitrogen).

```
ADJ012
5'-CGCGGATCCATGAAATATACAAGTTATATCTTGGCTTTTCAGCTCTGCATCGTTTT          (SEQ ID NO 16)

GGGTTCTCTTGGCTGTTACTGCCAAGATCCATATGTGAAAGAAGCT-3'
```

To clone IFNG in this expression vector, PCR amplification using ADJ012 and ADJ003 and pIGY-1 as template produces a 450 bp fragment that can be cloned in between BaMHI at the 5' end and XbaI at the 3' end of pcDNA3.1/hygra, giving rise to pIGY-5.

To introduce glycosylation sites in IFNG, oligonucleotides were designed in such a way that PCR generated changes could be introduced in the expression plasmid (pIGY-5) by classical two-step PCR followed by cloning the PCR fragment between BamHI at the 5' end and XbaI at the 3' end.

Therefore, two vector primers were designed to be used with specific mutation primers:

ADJ013 5'-GATGGCTGGCAACTAGAAG-3' (SEQ ID NO 17) (antisense downstream vector primer)

ADJ014 5'-TGTACGGTGGGAGGTCTAT-3' (SEQ ID NO 18) (sense upstream vector primer)

For the different muteins the following primers were designed.

K12T (SEQ ID NO 19)
ADJ015 5'-AGCATTAAAATACTTCGTCAAGTTTTCAGC-3'

(SEQ ID NO 20)
ADJ016 5'-GCTGAAAACTTGACGAAGTATTTTAATGCT-3'

G18T (SEQ ID NO 21)
ADJ017 5'-CACATCAGAATGAGTAGCATTAAAATA-3'

(SEQ ID NO 22)
ADJ018 5'-TATTTTAATGCTACTCATTCTGATGTG-3'

E38N (SEQ ID NO 23)
ADJ019 5'-CATAATTTTTCGATCGGATTCGTTTTTCCAATTCT-3'

(SEQ ID NO 24)
ADJ020 5'-AAGAATTGGAAAAACGAATCCGATCGAAAAATTATG-3'

K61T (SEQ ID NO 25)
ADJ021 5'-AATAGACTGATCGTCTGTAAAGTTTTTAAA-3'

(SEQ ID NO 26)
ADJ022 5'-TTTAAAAACTTTACAGACGATCAGTCTATT-3'

N85T (SEQ ID NO 27)
ADJ023 5'-TCTTTTCTTTTTAGTACTATTGAAAAACTT-3'

(SEQ ID NO 28)
ADJ024 5'-AAGTTTTCAATAGTACTAAAAAGAAAAGA-3'

K94N (SEQ ID NO 29)
ADJ025 5'-ATAATTAGTCAAATTTTCGAAGTCATG-3'

(SEQ ID NO 30)
ADJ026 5'-GATGACTTCGAAAATTTGACTAATTAT-3'

S99N (SEQ ID NO 31)
ADJ027 5'-AATCAAGTCAGTAACGTTATAATTAGTCAA-3'

(SEQ ID NO 32)
ADJ028 5'-TTGACTAATTATAACGTTACTGACTTGAAT-3'

Q106T (SEQ ID NO 33)
ADJ029 5'-ATGAATAGCTTTACTAGTCACATTCAAGTC-3'

(SEQ ID NO 34)
ADJ030 5'-GACTTGAATGTGACTAGTAAAGCTATTCAT-3'

After two step PCR and digestion with BamHI and XbaI each of these primer pairs are expected to result in a 447 bp fragrant that can be cloned in pIGY-5.

Expression of Interferon γ in CHO Cells

The above-mentioned construct are going to be transfected into the CHO K1 cell line (ATCC#CCL-61) by use of Lipofectamine 2000 (Life Technologies, USA) as tranfection agent 24 hours later the culture medium is going to be harvested and assayed for interferon γ activity and concentration.

The invention claimed is:

1. An E38N interferon gamma (IFNG) polypeptide variant exhibiting IFNG activity, comprising a polypeptide sequence which (i) differs by 1 to 15 amino acid residues from the wild-type human IFNG sequence shown in SEQ ID NO: 2 or a fragment thereof which is C-terminally truncated by 1 to 15 amino acid residues, and which (ii) comprises the substitution E38N.

2. The variant of claim 1, further comprising the substitution S40T.

3. The variant of claim 1, wherein the variant sequence differs by 1 to 8 amino acid residues fi m the wild-type human IFNG sequence shown in SEQ ID NO: 2 or a fragment thereof which is C-terminally truncated by 1 to 15 amino acid residues.

4. The variant of claim 3, wherein the variant sequence differs by 1 to 5 amino acid residues from the wild-type human IFNG sequence shown in SEQ ID NO: 2 or a fragment thereof which is C-terminally truncated by 1 to 15 amino acid residues.

5. The variant of claim 1, wherein the variant is C-terminally truncated by 11 amino acid residues.

6. The variant of claim 1, wherein the variant is glycosylated.

7. The variant of claim 6, wherein the variant is glycoslated at N25, N38 and N97.

8. The variant of claim 1, wherein the variant sequence differs by 3 amino acid residues from the wild-type human IFNG sequence shown in SEQ ID NO: 2 or a fragment thereof which is C-terminally truncated by 1 to 15 amino acid residues.

9. The variant of claim 8, further comprising the substitution S40T.

10. The variant of claim 9, wherein the variant is C-terminally truncated by 11 amino acid residues.

11. The variant of claim 10, wherein the variant is glycosylated.

12. The variant of claim 11, wherein the variant is glycosylated at N25, N38 and N97.

13. The variant of claim 1, wherein the variant comprises a cysteine residue, which is introduced into a position of the IFNG polypeptide that in wild-type human IFNG is occupied by a surface-exposed residue.

14. The variant of claim 13, wherein said introduced cysteine residue is PEGylated.

15. A pharmaceutical composition comprising the E38N interferon gamma polypeptide variant of claim 1 and a pharmaceutically acceptable diluent, carrier or adjuvant.

* * * * *

SEQUENCE LISTING

<160> NUMBER OF SEQ ID NOS: 34

<210> SEQ ID NO 1
<211> LENGTH: 166
<212> TYPE: PRT
<213> ORGANISM: Homo sapiens

<400> SEQUENCE: 1

Met Lys Tyr Thr Ser Tyr Ile Leu Ala Phe Gln Leu Cys Ile Val Leu
 1               5                  10                  15

Gly Ser Leu Gly Cys Tyr Cys Gln Asp Pro Tyr Val Lys Glu Ala Glu
             20                  25                  30

Asn Leu Lys Lys Tyr Phe Asn Ala Gly His Ser Asp Val Ala Asp Asn
         35                  40                  45

Gly Thr Leu Phe Leu Gly Ile Leu Lys Asn Trp Lys Glu Glu Ser Asp
     50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 2
<211> LENGTH: 143
<212> TYPE: PRT
<213> ORGANISM: Homo sapiens

<400> SEQUENCE: 2

Gln Asp Pro Tyr Val Lys Glu Ala Glu Asn Leu Lys Lys Tyr Phe Asn
 1               5                  10                  15

Ala Gly His Ser Asp Val Ala Asp Asn Gly Thr Leu Phe Leu Gly Ile
             20                  25                  30

Leu Lys Asn Trp Lys Glu Glu Ser Asp Arg Lys Ile Met Gln Ser Gln
         35                  40                  45

Ile Val Ser Phe Tyr Phe Lys Leu Phe Lys Asn Phe Lys Asp Asp Gln
     50                  55                  60

```
Ser Ile Gln Lys Ser Val Glu Thr Ile Lys Glu Asp Met Asn Val Lys
 65                  70                  75                  80

Phe Phe Asn Ser Asn Lys Lys Arg Asp Asp Phe Glu Lys Leu Thr
                 85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 3
<211> LENGTH: 375
<212> TYPE: DNA
<213> ORGANISM: Artificial Sequence
<220> FEATURE:
<223> OTHER INFORMATION: Description of Artificial Sequence: Expression
      cassette for expression of interferon gamma in
      yeast and CHO cells

<400> SEQUENCE: 3
tctgatgtgg ctgataatgg aactttgttc ttaggcattt tgaagaattg gaaagaagaa      60
tctgatagaa aaattatgca gtctcaaatt gtgtcttttt acttcaaatt gtttaaaaac     120
tttaaagatg atcagtctat tcaaaagtct gtggaaacta ttaaggaaga tatgaatgtg     180 aagttttca attctaacaa aaagaaaaga gatgacttcg aaaagttgac taattattct     240
gtgactgact tgaatgtgca agaaaagct attcatgaat tgatccaagt gatggctgaa     300
ttgtctccag ctgctaaaac aggaaagaga aaaagatctc agatgttgtt tagaggtaga     360
agagcttctc agtaa                                                     375

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 4
ggtttgatat cgatggccaa                                                 20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 5
gcggccctct agattact                                                   18

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 6
```
catctccgtc cactccgact ccatagcatg caagatccat atgtgaaaga a           51

<210> SEQ ID NO 7
<211> LENGTH: 84
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 7
atcttgcatg ctatggagtc ggagtggacg gagatggagt tggcggagta gaaggaaccg    60
ctgttttagc agctggagac aatt                                          84

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
ggtttgatat cgatggccaa                                               20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 9
gcggccctct agattact                                                 18

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
tttagaggta gaagagcttc tcagcaagat ccatatgtga agaagct                 48

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 11
agcttctttc acatatggat cttgctgaga agctcttcta cgtctaaa                48

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 12
tgctctagac atctgagatc gttttctctt tcc                          33

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
ggtttgatat cgatggccaa                                         20

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 14
catctccgtc cactccgact ccatagcatg caagatccat atgtgaaaga a       51

<210> SEQ ID NO 15
<211> LENGTH: 81
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 15
atcttgcatg ctatggagtc ggagtggacg gagatggagt tggcggagta aaggaaccg   60 gcatctgaga tcttttttctc c                                      81

<210> SEQ ID NO 16
<211> LENGTH: 102
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
cgcggatcca tgaaatatac aagttatatc ttggcttttc agctctgcat cgttttgggt   60
tctcttggct gttactgcca agatccatat gtgaaagaag ct                 102

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 17
gatggctggc aactagaag                                          19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic PCR primer

<400> SEQUENCE: 18
tgtacggtgg gaggtctat                                                19

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 19
agcattaaaa tacttcgtca agttttcagc                                    30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 20
gctgaaaact tgacgaagta ttttaatgct                                    30

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 21
cacatcagaa tgagtagcat taaaata                                       27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 22
tattttaatg ctactcattc tgatgtg                                       27

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 23
cataattttt cgatcggatt cgttttccca attctt                             36

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      PCR primer

```
<400> SEQUENCE: 24
aagaattgga aaaacgaatc cgatcgaaaa attatg                                    36

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 25
aatagactga tcgtctgtaa agtttttaaa                                           30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Snythetic
      PCR primer

<400> SEQUENCE: 26
tttaaaaact ttacagacga tcagtctatt                                           30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 27
tcttttcttt ttagtactat tgaaaaactt                                           30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 28
aagtttttca atagtactaa aagaaaaga                                            30

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 29
ataattagtc aaattttcga agtcatg                                              27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer
```

```
-continued

<400> SEQUENCE: 30
gatgacttcg aaaatttgac taattat                                       27

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 31
aatcaagtca gtaacgttat aattagtcaa                                    30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 32
ttgactaatt ataacgttac tgacttgaat                                    30

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 33
atgaatagct ttactagtca cattcaagtc                                    30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 34
gacttgaatg tgactagtaa agctattcat                                    30
```